US010172305B2

(12) United States Patent
Yates et al.

(10) Patent No.: US 10,172,305 B2
(45) Date of Patent: Jan. 8, 2019

(54) DIAGNOSTIC MOLECULAR MARKERS FOR SEED LOT PURITY TRAITS IN SOYBEANS

(75) Inventors: Jennifer Yates, St. Louis, MO (US); Holly Kleiss, St. Louis, MO (US); John P. Tamulonis, Woodland, CA (US); David R. Wooten, Jr., Middletown, DE (US); Kunsheng Wu, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 1372 days.

(21) Appl. No.: 14/114,642

(22) PCT Filed: Apr. 26, 2012

(86) PCT No.: PCT/US2012/035259
§ 371 (c)(1),
(2), (4) Date: Jan. 7, 2014

(87) PCT Pub. No.: WO2012/149193
PCT Pub. Date: Nov. 1, 2012

(65) Prior Publication Data
US 2014/0115732 A1    Apr. 24, 2014

Related U.S. Application Data

(60) Provisional application No. 61/480,590, filed on Apr. 29, 2011.

(51) Int. Cl.
*A01H 1/04* (2006.01)
*A01H 5/10* (2018.01)
*C07K 14/415* (2006.01)
*C12N 9/02* (2006.01)

(52) U.S. Cl.
CPC ............... *A01H 1/04* (2013.01); *A01H 5/10* (2013.01); *C07K 14/415* (2013.01); *C12N 9/0073* (2013.01); *C12Y 114/13088* (2013.01)

(58) Field of Classification Search
None
See application file for complete search history.

(56) References Cited

U.S. PATENT DOCUMENTS

| | | |
|---|---|---|
| 5,210,015 A | 5/1993 | Gelfand et al. |
| 5,217,863 A | 6/1993 | Cotton et al. |
| 5,468,613 A | 11/1995 | Erlich et al. |
| 5,595,890 A | 1/1997 | Newton et al. |
| 5,616,464 A | 4/1997 | Albagli et al. |
| 5,762,876 A | 6/1998 | Lincoln et al. |
| 5,800,944 A | 9/1998 | Blonsky et al. |
| 5,876,930 A | 3/1999 | Livak et al. |
| 5,945,283 A | 8/1999 | Kwok et al. |
| 6,004,744 A | 12/1999 | Goelet et al. |
| 6,013,431 A | 1/2000 | Soderlund et al. |
| 6,030,787 A | 2/2000 | Livak et al. |
| 6,090,558 A | 7/2000 | Butler et al. |
| 6,207,367 B1 | 3/2001 | Helentjaris et al. |
| 6,503,710 B2 | 1/2003 | Gut et al. |
| 6,613,509 B1 | 9/2003 | Chen |
| 6,799,122 B2 | 9/2004 | Benson |
| 6,913,879 B1 | 7/2005 | Schena |
| 6,996,476 B2 | 2/2006 | Najarian |
| 7,238,476 B2 | 7/2007 | McKeown et al. |
| 7,250,252 B2 | 7/2007 | Katz et al. |
| 7,270,981 B2 | 9/2007 | Armes et al. |
| 7,282,355 B2 | 10/2007 | Shi |
| 7,297,485 B2 | 11/2007 | Bornarth et al. |
| 7,312,039 B2 | 12/2007 | Barany et al. |
| 7,649,127 B2 * | 1/2010 | Eby ................ A01H 5/10 435/415 |
| 2005/0204780 A1 | 9/2005 | Moridaira et al. |
| 2005/0216545 A1 | 9/2005 | Aldrich et al. |
| 2005/0218305 A1 | 10/2005 | Tsukamoto et al. |
| 2006/0288444 A1 | 12/2006 | McCarroll et al. |

FOREIGN PATENT DOCUMENTS

WO    2009108513 A2    9/2009

OTHER PUBLICATIONS

Zabala et al. (cited in IDS, The Plant Genome, Jul. 2007, pp. 113-124).*
Iwashina et al. (cited in IDS, Journal of Heredity, 2006, pp. 438-443).*
Ballester et al. (Euphytica 103: pp. 223-226, 1998).*
Yang et al. (Journal of Heredity 2010: 101(6): pp. 757-768).*
Chung et al 2003 Crop Sci. 43:1053-1067 (Year: 2003).*
Iwashina et al 2006 97:438-443 (Year: 2006).*
Shultz et al., "A Soybean Mapping Population Specific to the Early Soybean Production System", DNA Sequence, 2007, pp. 104-111, vol. 18, No. 2.
Iwashina et al., "Analysis of Flavonoids in Pubescence of Soybean Near-Isogenic Lines for Pubescence Color Loci", Journal of Heredity, 2006, pp. 438-443, vol. 97, No. 5.
Zabala et al., "A Rearrangement Resulting in Small Tandem Repeats in the F3'5'H Gene of White Flower in Genotypes is Associated with the Soybean W1 Locus", Crop Science, 2007, pp. S113-S124, vol. 47, No. S2.
Yang et al., Genetic Analysis of Genes Controlling Natural Variation of Seed Coat and Flower Colors in Soybean, Journal of Heredity, 2010, pp. 757-768, vol. 101, No. 6.
Database EMBL (Online), "Glycine Max Flavonoid 3'5' Hydroxylase (w1) Gene, Complete CDs", Jun. 9, 2007, XP002680560, Retrieved from EBI, Database Accession No. EF174666.

(Continued)

*Primary Examiner* — Brent T Page
(74) *Attorney, Agent, or Firm* — Thompson Coburn LLP; William A. Holtz; Amanda J. Carmany-Rampey

(57) ABSTRACT

The present invention is in the field of plant breeding. More specifically, the invention includes a method for breeding and selecting plants that uniform for one or more seed lot purity traits such as, such as distinct flower color, pubescence color, hilum color, and pod wall color. The invention further includes molecular markers associated with distinct flower color, pubescence color, hilum color, and pod wall color for uses in a breeding program.

4 Claims, No Drawings

Specification includes a Sequence Listing.

(56) References Cited

OTHER PUBLICATIONS

Database EMBL (Online), "Glycine Max Flavonoid 3'5' Hydroxylase (W1) Gene, Complete CDs", Jun. 9, 2007, XP002680561, Retrieved from EBI, Database Accession No. EF174665.
Barwale et al., "Plant regeneration from callus cultures of several soybean genotypes via embryogenesis and organogenesis", Planta, 1986, pp. 473-481, vol. 167.
Borevitz et al., "Large-Scale Identification of Single-Feature Polymorphisms in Complex Genomes", Genome Research, 2003, pp. 513-523, vol. 13, Cold Spring Harbor Laboratory Press.
Kameya et al., "Plant Regeneration from Hypocotyl Sections of Glycine Species", Plant Science Letters, 1981, pp. 289-294, vol. 21.
Kartha et al., "Plant regeneration from meristems of grain legumes: soybean, cowpea, peanut, chickpea, and bean", Canadian Journal of Botany, 1981, pp. 1671-1679, vol. 59.
Cheng et al., "Plant Regeneration from Soybean Cotyledonary Node Segments in Culture", Plant Science Letters, 1980, pp. 91-99, vol. 19.
Cui et al., "Detecting Single-Feature Polymorphisms Using Oligonucleotide Arrays and Robustified Projection Pursuit", Bioinformatics, 2005, pp. 3852-3858, vol. 21, No. 20, Oxford University Press.
Fehr, Walter R., "Breeding", Soybean Physiology, Agronomy, and Utilization, 1978, pp. 119-155. Academic Press, New York.
Service, Robert F., "Gene Sequencing: The Race for the $1000 Genome", Science, 2006, pp. 1544-1546, vol. 311.
Ranch et al., "Plant Regeneration from Embryo-Derived Tissue Cultures of Soybeans", In Vitro Cellular & Developmental Biology, Nov. 1985, pp. 653-658, vol. 21 No. 11.
Saka et al., "Stimulation of Multiple Shoot Formation on Soybean Stem Nodes in Culture", Plant Science Letters, 1980, pp. 193-201, vol. 19.
Widholm, J.M., "In vitro Selection and Culture-induced Variation in Soybean", Soybean: Genetics, Molecular Biology and Biotechnology, 1996, pp. 107-126, CAB International, Wallingford, Oxon, England.
Wright et al., "Plant regeneration by organogenesis in Glycine max", Plant Cell Reports, 1986, pp. 150-154, vol. 5.

\* cited by examiner

DIAGNOSTIC MOLECULAR MARKERS FOR SEED LOT PURITY TRAITS IN SOYBEANS

CROSS-REFERENCE TO RELATED APPLICATION

This application is a 35 U.S.C. § 371 application of PCT/US2012/035259 filed Apr. 26, 2012, which claims priority to U.S. Provisional Application Ser. No. 61/480,590 filed Apr. 29, 2011, each of which are incorporated herein by reference in its entirety.

INCORPORATION OF SEQUENCE LISTING

A sequence listing containing the file named "46_21_57028_A_PCT.txt" which is 37,927 bytes (measured in MS-Windows®) and created on Apr. 26, 2012, comprises 62 nucleotide sequences, and is herein incorporated by reference in its entirety.

INCORPORATION OF APPENDIX

A listing of various soybean genomic markers is provided herewith in an Appendix to the Specification as Table 14 (17640 bytes measured in MS-Windows®) and is herein incorporated by reference in its entirety.

BACKGROUND OF THE INVENTION

The present invention relates to a method for characterizing phenotypic traits of soybean varieties important for seed lot purity. More specifically, the invention relates to the use of molecular markers to select for the seed lot purity traits of flower color, pubescence color, hilum color, and pod wall color in soybean varieties.

Seed lot purity in commercial soybean seed lots is of particular importance to both seed consumers and seed producers. Seed consumers want to purchase a product with seeds of similar or identical characteristics related to species, variety, genetics, and germination rates. Seed producers want confidence in their soybean breeding programs to select for desired seed lot purity traits. Unfortunately, uncontrollable environmental factors may result in significant phenotypic variation for these seed lot purity traits resulting in breeding error selections. Therefore, a method to reliably select for seed lot purity traits during soybean seed production is critical for the evaluation of plants for promotion in soybean breeding programs to produce consistent seed lot for commercialization. The method to use molecular markers for the seed lot purity traits of flower color, pubescence color, hilum color, and pod wall color provides more consistent and reliable data to evaluate certain traits important for seed lot purity.

SUMMARY OF THE INVENTION

In certain embodiments of the invention, a soybean plant comprising a genotype associated with a desired flower color phenotype is identified by:
a) obtaining a DNA or RNA sample from a tissue of at least one soybean plant;
b) determining whether the allelic state of the soybean plant comprises the allelic form represented by SEQ ID NO:1 or SEQ ID NO:2; and
c) identifying at least one soybean plant in which the allelic state determined is associated with the desired flower color.

Certain other embodiments of the invention are related to methods of, for example, selecting, introgressing, predicting, validating, obtaining, or producing a soybean plant, comprising these steps.

In certain embodiments of the invention, a soybean plant comprising a genotype associated with a desired pubescence color phenotype is identified by:
a) obtaining a DNA or RNA sample from a tissue of at least one soybean plant;
b) determining the allelic state of the molecular marker represented by SEQ ID NO:8 (M0243191);
c) determining whether the allelic state of the soybean plant comprises the allelic form represented by SEQ ID NO:13 or SEQ ID NO:14; and
d) identifying at least one soybean plant in which the allelic state determined in steps b) and c) is associated with the desired pubescence color.

Certain other embodiments of the invention are related to methods of, for example, selecting, introgressing, predicting, validating, obtaining, or producing a soybean plant, comprising these steps.

In certain embodiments of the invention, a soybean plant comprising a genotype associated with a desired hilum color phenotype is identified by:
a) obtaining a DNA or RNA sample from a tissue of at least one soybean plant;
b) determining the allelic state of the molecular marker represented by SEQ ID NO:19 (M0100925); and
c) identifying at least one soybean plant in which the allelic state determined is associated with the desired hilum color.

Certain other embodiments of the invention are related to methods of, for example, selecting, introgressing, predicting, validating, obtaining, or producing a soybean plant, comprising these steps.

In certain embodiments of the invention, a soybean plant comprising a genotype associated with a desired pod wall color phenotype is identified by:
a) obtaining a DNA or RNA sample from a tissue of at least one soybean plant;
b) determining the allelic state of the haplotype defined by the molecular markers represented by SEQ ID NO:26 (M0202726), SEQ ID NO:33 (M0119618), and SEQ ID NO:40 (M0094170); and
c) identifying at least one soybean plant in which the allelic state determined is associated with the desired pod wall color.

Certain other embodiments of the invention are related to methods of, for example, selecting, introgressing, predicting, validating, obtaining, or producing a soybean plant, comprising these steps.

In certain embodiments of the invention, a soybean plant comprising a genotype associated with a desired pubescence color phenotype is identified by:
a) obtaining a DNA or RNA sample from a tissue of at least one soybean plant;
b) determining the allelic state of the molecular marker represented by SEQ ID NO:8 (M0243191);
c) determining the allelic state of the haplotype defined by the molecular markers represented by SEQ ID NO:53 (M006200746) and SEQ ID NO:54 (M006200926); and
d) identifying at least one soybean plant in which the allelic state determined is associated with the desired pubescence color.

Certain other embodiments of the invention are related to methods of, for example, selecting, introgressing, predicting, validating, obtaining, or producing a soybean plant, comprising these steps.

In certain embodiments of the invention, a soybean plant comprising a genotype associated with a desired hilum color phenotype is identified by:
  a) obtaining a DNA or RNA sample from a tissue of at least one soybean plant;
  b) determining the allelic state of the haplotype defined by the molecular markers represented by SEQ ID NO:55 (M006725263), SEQ ID NO:56 (M006725275), SEQ ID NO:57 (M006725283), SEQ ID NO:58 (M006934394), SEQ ID NO:59 (M006934399), SEQ ID NO:60 (M006934436), SEQ ID NO:61 (M006934505), and SEQ ID NO:62 (M006934661); and
  c) identifying at least one soybean plant in which the allelic state determined is associated with the desired hilum color.

Certain other embodiments of the invention are related to methods of, for example, selecting, introgressing, predicting, validating, obtaining, or producing a soybean plant, comprising these steps.

In certain embodiments of the invention, a soybean plant comprising a genotype associated with a desired pod wall color phenotype is identified by:
  a) obtaining a DNA or RNA sample from a tissue of at least one soybean plant;
  b) determining the allelic state of the haplotype defined by the molecular markers represented by SEQ ID NO:47 (M006065284), SEQ ID NO:48 (M006065312), SEQ ID NO:49 (M006065346), SEQ ID NO:50 (M006065360), SEQ ID NO:51 (M006065367), and SEQ ID NO:52 (006065379); and
  c) identifying at least one soybean plant in which the allelic state determined is associated with the desired pod wall color.

Certain other embodiments of the invention are related to methods of, for example, selecting, introgressing, predicting, validating, obtaining, or producing a soybean plant, comprising these steps.

In certain embodiments of the invention, soybean plant comprising a genotype associated with a gray pubescence color phenotype is identified by:
  a) obtaining a DNA or RNA sample from a tissue of at least one soybean plant;
  b) determining the allelic state of the molecular marker represented by SEQ ID NO:8 (M0243191); and
  c) identifying at least one soybean plant comprising the TT allelic state of the molecular marker represented by SEQ ID NO:8, thereby identifying a soybean plant comprising a genotype associated with a gray pubescence color.

Certain other embodiments of the invention are related to methods of, for example, selecting, introgressing, predicting, validating, obtaining, or producing a soybean plant, comprising these steps.

In certain embodiments of the invention, molecular markers associated with a phenotype are identified within a genomic region of a linkage group associated with a desired phenotype, such as a genomic region flanked by certain other molecular markers.

In certain embodiments of the invention, a soybean plant comprising a genotype associated with a desired hilum color phenotype is identified by:
  a) obtaining a DNA or RNA sample from a tissue of at least one soybean plant;
  b) determining the allelic state of at least one molecular marker associated with hilum color, wherein the molecular marker is in a linkage group K genomic region flanked by loci AI973910 (SEQ ID NO:20) and BG045318 (SEQ ID NO:21); and
  c) identifying at least one soybean plant in which the allelic state determined is associated with the desired hilum color.

Certain other embodiments of the invention are related to methods of, for example, selecting, introgressing, predicting, validating, obtaining, or producing a soybean plant, comprising these steps.

In certain embodiments of the invention, a soybean plant comprising a genotype associated with a desired pod wall color phenotype is identified by:
  a) obtaining a DNA or RNA sample from a tissue of at least one soybean plant;
  b) determining the allelic state of at least one molecular marker associated with pod wall color, wherein the molecular marker is in a linkage group N genomic region flanked by loci AW459958 (SEQ ID NO:27) and AW755424 (SEQ ID NO:28);
  c) determining the allelic state of at least one molecular marker associated with pod wall color, wherein the molecular marker is in a linkage group N genomic region flanked by loci BF597543 (SEQ ID NO:34) and BU550813 (SEQ ID NO:35);
  d) determining the allelic state of at least one molecular marker associated with pod wall color, wherein the molecular marker is in a linkage group N genomic region flanked by loci BF597543 (SEQ ID NO:41) and TA53077 (SEQ ID NO:42); and
  e) identifying at least one soybean plant in which the allelic state determined in steps b), c) and d) is associated with the desired pod wall color.

Certain other embodiments of the invention are related to methods of, for example, selecting, introgressing, predicting, validating, obtaining, or producing a soybean plant, comprising these steps.

In certain embodiments, the homogeneity in successive generations of a population of soybean plants is increased by:
  a) crossing two parental soybean plants to generate an $F_1$ population of soybean plants;
  b) self-crossing at least one soybean plant of the $F_1$ population to generate an $F_2$ population of soybean plants;
  c) obtaining a DNA or RNA sample from a tissue of at least one soybean plant of the $F_2$ population;
  d) (i) determining whether the allelic state of the soybean plant comprises the allelic form represented by SEQ ID NO:1 or SEQ ID NO:2;
    (ii) determining the allelic state of the molecular marker represented by SEQ ID NO:8 (M0243191);
    (iii) determining whether the allelic state of the soybean plant comprises the allelic form represented by SEQ ID NO:13 or SEQ ID NO:14;
    (iv) determining the allelic state of the molecular marker represented by SEQ ID NO:19 (M0100925);
    (v) determining the allelic state of the haplotype defined by the molecular markers represented by SEQ ID NO:26 (M0202726), SEQ ID NO:33 (M0119618), and SEQ ID NO:40 (M0094170); and
  e) selecting at least one plant of the $F_2$ population based on the allelic state determined in step (d) and self-crossing the selected plant to generate an $F_3$ population of soybean plants; thus increasing the homogeneity of successive generations.

This method can be extended by repeating steps c) and d) with at least one plant of the $F_3$ population, wherein at least one plant of the $F_3$ is selected based on the determined allelic state, and wherein the selected plant is self-crossed to generate an $F_4$ population of soybean plants. In certain embodiments the method can be extended to $F_4$, $F_5$, $F_6$ or higher generations.

In certain embodiments, the homogeneity in successive generations of a population of soybean plants is increased by:
 a) crossing two parental soybean plants to generate an $F_1$ population of soybean plants;
 b) self-crossing at least one soybean plant of the $F_1$ population to generate an F2 population of soybean plants;
 c) obtaining a DNA or RNA sample from a tissue of at least one soybean plant of the $F_2$ population;
 d) (i) determining whether the allelic state of the soybean plant comprises the allelic form represented by SEQ ID NO:1 or SEQ ID NO:2;
  (ii) determining the allelic state of the molecular marker represented by SEQ ID NO:8 (M0243191);
  (iii) determining whether the allelic state of the soybean plant comprises the allelic form represented by SEQ ID NO:13 or SEQ ID NO:14;
  (iv) determining the allelic state of at least one molecular marker associated with hilum color, wherein the polymorphic marker is in a linkage group K genomic region flanked by loci AI973910 (SEQ ID NO:20) and BG045318 (SEQ ID NO:21);
  (v) determining the allelic state of at least one molecular marker associated with pod wall color, wherein the molecular marker is in a linkage group N genomic region flanked by loci AW459958 (SEQ ID NO:27) and AW755424 (SEQ ID NO:28), determining the allelic state of at least one molecular marker associated with pod wall color, wherein the molecular marker is in a linkage group N genomic region flanked by loci BF597543 (SEQ ID NO:34) and BU550813 (SEQ ID NO:35), and determining the allelic state of at least one molecular marker associated with pod wall color, wherein the molecular marker is in a linkage group N genomic region flanked by loci BF597543 (SEQ ID NO:41) and TA53077 (SEQ ID NO:42); and
 e) selecting at least one plant of the $F_2$ population based on the allelic state determined in step (d) and self-crossing the selected plant to generate an $F_3$ population of soybean plants; thus increasing the homogeneity of successive generations.

This method can be extended by repeating steps c) and d) with at least one plant of the $F_3$ population, wherein at least one plant of the $F_3$ is selected based on the determined allelic state, and wherein the selected plant is self-crossed to generate an $F_4$ population of soybean plants. In certain embodiments the method can be extended to $F_4$, $F_5$, $F_6$ or higher generations.

In certain embodiments, the homogeneity in successive generations of a population of soybean plants is increased by:
 a) crossing two parental soybean plants to generate an $F_1$ population of soybean plants;
 b) self-crossing at least one soybean plant of the $F_1$ population to generate an $F_2$ population of soybean plants;
 c) obtaining a DNA or RNA sample from a tissue of at least one soybean plant of the $F_2$ population;
 d) (i) determining whether the allelic state of the soybean plant comprises the allelic form represented by SEQ ID NO:1 or SEQ ID NO:2;
  (ii) determining the allelic state of the molecular marker represented by SEQ ID NO:8 (M0243191);
  (iii) determining the allelic state of the haplotype defined by the molecular markers represented by SEQ ID NO:53 (M006200746) and SEQ ID NO:54 (M006200926);
  (iv) determining the allelic state of the haplotype defined by the molecular markers represented by SEQ ID NO:55 (M006725263), SEQ ID NO:56 (M006725275), SEQ ID NO:57 (M006725283), SEQ ID NO:58 (M006934394), SEQ ID NO:59 (M006934399), SEQ ID NO:60 (M006934436), SEQ ID NO:61 (M006934505), and SEQ ID NO:62 (M006934661);
  (v) determining the allelic state of the haplotype defined by the molecular markers represented by SEQ ID NO:47 (M006065284), SEQ ID NO:48 (M006065312), SEQ ID NO:49 (M006065346), SEQ ID NO:50 (M006065360), SEQ ID NO:51 (M006065367), and SEQ ID NO:52 (006065379); and
 e) selecting at least one plant of the $F_2$ population based on the allelic state determined in step (d) and self-crossing the selected plant to generate an $F_3$ population of soybean plants; thus increasing the homogeneity of successive generations.

This method can be extended by repeating steps c) and d) with at least one plant of the $F_3$ population, wherein at least one plant of the $F_3$ is selected based on the determined allelic state, and wherein the selected plant is self-crossed to generate an $F_4$ population of soybean plants. In certain embodiments the method can be extended to $F_4$, $F_5$, $F_6$ or higher generations.

The present invention relates to molecular markers for the seed lot purity traits of flower color, pubescence color, hilum color and pod wall color. These molecular markers can reduce the time associated with purifying the varieties, selecting sub lines that vary in morphological characteristics and evaluating selfing and outcrossing of plants.

Certain embodiments of the invention comprise, selecting seeds comprising a genotype associated with a distinct flower color, pubescence color, hilum color and pod wall color. It is understood that although certain embodiments combining the identification of certain genotypes are expressly disclosed, other combinations of the genotypes and corresponding phenotypes disclosed herein are contemplated.

The present invention includes methods for introgressing alleles into a soybean plant comprising (a) crossing at least a first soybean plant with at least a second soybean plant in order to form a segregating population, (b) screening the segregating population with one or more nucleic acid markers selected from the group comprising a nucleic acid sequence selected from the group consisting of SEQ ID NO: 1 through SEQ ID NO: 62 to determine if one or more soybean plants from the segregating population contains a listed nucleic acid sequence, and (c) selecting from that segregating population one or more soybean plants comprising a nucleic acid sequence selected from the group comprising a nucleic acid sequence selected from the group consisting of SEQ ID NO: 1 through SEQ ID NO: 62.

The present invention includes methods for introgressing alleles and selecting for morphological traits, including flower color, pubescence color, hilum color and pod wall color of a soybean plant comprising (a) crossing at least one soybean plant with a second soybean plant in order to form a segregating population and (b) screening the segregating population with one or more nucleic acid markers to determine if one or more soybean plants from the segregating population contain alleles of genomic region associated with morphological traits, including flower color, pubescence color, hilum color and pod wall color.

The present invention further provides a method for selection and introgression of genomic regions associated with morphological traits, including flower color, pubescence color, hilum color and pod wall color comprising: (a) isolating nucleic acids from a plurality of soybean plants; (b) detecting in the isolated nucleic acids the presence of one or more marker molecules wherein the marker molecule is selected from the group consisting of SEQ ID NO: 1 through SEQ ID NO: 62, and any one marker molecule mapped within 30 cM or less from the marker molecules; and (c) selecting a soybean plant comprising the one or more marker molecules, thereby selecting a soybean plant.

Plant parts are also provided by the invention. Parts of a plant of the invention include, but are not limited to, pollen, ovules, meristems, cells, and seed. Cells of the invention may further comprise, regenerable cells, such as embryos meristematic cells, pollen, leaves, roots, root tips, and flowers. Thus, these cells could be used to regenerate plants of the invention.

In yet a further aspect of the invention there is provided a method for producing a soybean seed, comprising crossing the plant of the invention with itself or with a second soybean plant. Thus, this method may comprise preparing a hybrid soybean seed by crossing a plant of the invention with a second, distinct, soybean plant.

In further embodiments, a plant of the invention may further comprise a transgene. The transgene may in one embodiment be defined as conferring a preferred property to the soybean plant selected from the group consisting of herbicide tolerance, increased yield, insect control, fungal disease resistance, virus resistance, nematode resistance, bacterial disease resistance, mycoplasma disease resistance, altered fatty acid composition, altered oil production, altered amino acid composition, altered protein production, increased protein production, altered carbohydrate production, germination and seedling growth control, enhanced animal and human nutrition, low raffinose, drought and/or environmental stress tolerance, altered morphological characteristics, increased digestibility, industrial enzymes, pharmaceutical proteins, peptides and small molecules, improved processing traits, improved flavor, nitrogen fixation, hybrid seed production, reduced allergenicity, biopolymers, biofuels, or any combination of these.

Embodiments discussed in the context of a method and/or composition of the invention may be employed with respect to any other method or composition described herein. Thus, an embodiment pertaining to one method or composition may be applied to other methods and compositions of the invention as well.

Further objects, features and advantages of the present invention will become apparent from the following detailed description. It should be understood, however, that the description and the specific examples are given by way of illustration only and are not intended to limit the scope of the present disclosure. Various changes and modifications within the spirit and scope of the invention will become apparent to those skilled in the art from this detailed description.

DESCRIPTION OF NUCLEIC ACID SEQUENCES

SEQ ID NO: 1 is a genomic sequence derived from Glycine max associated with the flavonoid 3'5' hydroxylase gene representing the W1 allele.

SEQ ID NO: 2 is a genomic sequence derived from Glycine max associated with the flavonoid 3'5' hydroxylase gene representing the w1 allele.

SEQ ID NO: 3 is a genomic sequence derived from Glycine max associated with the flavonoid 3'5' hydroxylase gene and representing a 10 base pair substitution in the w1 allele.

SEQ ID NO: 4 is a forward PCR primer for the amplification of SEQ ID NO: 2.

SEQ ID NO: 5 is a reverse PCR primer for the amplification of SEQ ID NO: 2.

SEQ ID NO: 6 is a probe for the detection of the substitution in the w1 allele of SEQ ID NO: 2.

SEQ ID NO: 7 is a probe for the detection of the substitution in the w1 allele of SEQ ID NO: 2.

SEQ ID NO: 8 is a genomic sequence of a molecular marker (M0243191) derived from Glycine max associated with the T locus.

SEQ ID NO: 9 is a forward PCR primer for the amplification of SEQ ID NO: 8.

SEQ ID NO: 10 is a reverse PCR primer for the amplification of SEQ ID NO: 8.

SEQ ID NO: 11 is a probe for the detection of the molecular marker of SEQ ID NO: 8.

SEQ ID NO: 12 is a probe for the detection of the molecular marker of SEQ ID NO: 8.

SEQ ID NO: 13 is a genomic sequence derived from Glycine max associated with the Td locus.

SEQ ID NO: 14 is a genomic sequence derived from Glycine max associated with a nucleotide deletion in the Td locus.

SEQ ID NO: 15 is a forward PCR primer for the amplification of SEQ ID NO: 14.

SEQ ID NO: 16 is a reverse PCR primer for the amplification of SEQ ID NO: 14.

SEQ ID NO: 17 is a probe for the detection of the molecular marker of SEQ ID NO: 14.

SEQ ID NO: 18 is a probe for the detection of the molecular marker of SEQ ID NO: 14.

SEQ ID NO: 19 is a genomic sequence of a molecular marker (M0100925) derived from Glycine max associated with the R locus.

SEQ ID NO: 20 is a genomic sequence of a molecular marker derived from Glycine max associated with the R locus. (see Appendix)

SEQ ID NO: 21 is a genomic sequence of a molecular marker derived from Glycine max associated with the R locus. (see Appendix)

SEQ ID NO: 22 is a forward PCR primer for the amplification of SEQ ID NO: 19.

SEQ ID NO: 23 is a reverse PCR primer for the amplification of SEQ ID NO: 19.

SEQ ID NO: 24 is a probe for the detection of the molecular marker of SEQ ID NO: 19.

SEQ ID NO: 25 is a probe for the detection of the molecular marker of SEQ ID NO: 19.

SEQ ID NO: 26 is a genomic sequence of a molecular marker (M0202726) derived from Glycine max associated with the L2 locus.

SEQ ID NO: 27 is a genomic sequence of a molecular marker derived from Glycine max associated with the L2 locus. (see Appendix)

SEQ ID NO: 28 is a genomic sequence of a molecular marker derived from Glycine max associated with the L2 locus. (see Appendix)

SEQ ID NO: 29 is a forward PCR primer for the amplification of SEQ ID NO: 26.

SEQ ID NO: 30 is a reverse PCR primer for the amplification of SEQ ID NO: 26.

SEQ ID NO: 31 is a probe for the detection of the molecular marker of SEQ ID NO: 26.

SEQ ID NO: 32 is a probe for the detection of the molecular marker of SEQ ID NO: 26.

SEQ ID NO: 33 is a genomic sequence of a molecular marker (M0119618) derived from *Glycine max* associated with the L2 locus.

SEQ ID NO: 34 is a genomic sequence of a molecular marker derived from *Glycine max* associated with the L2 locus. (see Appendix)

SEQ ID NO: 35 is a genomic sequence of a molecular marker derived from *Glycine max* associated with the L2 locus. (see Appendix)

SEQ ID NO: 36 is a forward PCR primer for the amplification of SEQ ID NO: 33.

SEQ ID NO: 37 is a reverse PCR primer for the amplification of SEQ ID NO: 33.

SEQ ID NO: 38 is a probe for the detection of the molecular marker of SEQ ID NO: 33.

SEQ ID NO: 39 is a probe for the detection of the molecular marker of SEQ ID NO: 33.

SEQ ID NO: 40 is a genomic sequence of a molecular marker (M0094170) derived from *Glycine max* associated with the L2 locus.

SEQ ID NO: 41 is a genomic sequence of a molecular marker derived from *Glycine max* associated with the L2 locus. (see Appendix)

SEQ ID NO: 42 is a genomic sequence of a molecular marker derived from *Glycine max* associated with the L2 locus. (see Appendix)

SEQ ID NO: 43 is a forward PCR primer for the amplification of SEQ ID NO: 40.

SEQ ID NO: 44 is a reverse PCR primer for the amplification of SEQ ID NO: 40.

SEQ ID NO: 45 is a probe for the detection of the molecular marker of SEQ ID NO: 40.

SEQ ID NO: 46 is a probe for the detection of the molecular marker of SEQ ID NO: 40.

SEQ ID NO: 47 is a genomic sequence of a molecular marker (M006065284) derived from *Glycine max* associated with the L2 locus.

SEQ ID NO: 48 is a genomic sequence of a molecular marker (M006065312) derived from *Glycine max* associated with the L2 locus.

SEQ ID NO: 49 is a genomic sequence of a molecular marker (M006065346) derived from *Glycine max* associated with the L2 locus.

SEQ ID NO: 50 is a genomic sequence of a molecular marker (M006065360) derived from *Glycine max* associated with the L2 locus.

SEQ ID NO: 51 is a genomic sequence of a molecular marker (M006065367) derived from *Glycine max* associated with the L2 locus.

SEQ ID NO: 52 is a genomic sequence of a molecular marker (M006065379) derived from *Glycine max* associated with the L2 locus.

SEQ ID NO: 53 is a genomic sequence of a molecular marker (M006200746) derived from *Glycine max* associated with the Td locus.

SEQ ID NO: 54 is a genomic sequence of a molecular marker (M006200926) derived from *Glycine max* associated with the Td locus.

SEQ ID NO: 55 is a genomic sequence of a molecular marker (M006725263) derived from *Glycine max* associated with the I locus.

SEQ ID NO: 56 is a genomic sequence of a molecular marker (M006725275) derived from *Glycine max* associated with the I locus.

SEQ ID NO: 57 is a genomic sequence of a molecular marker (M006725283) derived from *Glycine max* associated with with the I locus.

SEQ ID NO: 58 is a genomic sequence of a molecular marker (M006934394) derived from *Glycine max* associated with the with the R locus.

SEQ ID NO: 59 is a genomic sequence of a molecular marker (M006934399) derived from *Glycine max* associated with the R locus.

SEQ ID NO: 60 is a genomic sequence of a molecular marker (M006934436) derived from *Glycine max* associated with the R locus.

SEQ ID NO: 61 is a genomic sequence of a molecular marker (M006934505) derived from *Glycine max* associated with the R locus.

SEQ ID NO: 62 is a genomic sequence of a molecular marker (M006934661) derived from *Glycine max* associated with the R locus.

I. DESCRIPTION OF THE INVENTION: DEFINITIONS

The definitions and methods provided define the present invention and guide those of ordinary skill in the art in the practice of the present invention. Unless otherwise noted, terms are to be understood according to conventional usage by those of ordinary skill in the relevant art. Definitions of common terms in molecular biology may also be found in Alberts et al., Molecular Biology of The Cell, 5$^{th}$ Edition, Garland Science Publishing, Inc.: New York, 2007; and Lewin, Genes IX, Oxford University Press: New York, 2007. The nomenclature for DNA bases as set forth at 37 CFR § 1.822 is used.

As used herein, an "allele" refers to one of at least two alternative forms of a genomic sequence at a given locus on a chromosome.

As used herein, a "homozygous allele" is a locus on a chromosome having identical alleles for a signal trait.

As used herein, a "heterozygous allele" is a locus on a chromosome having two different alleles for a signal trait.

As used herein, a "locus" is a position on a genomic sequence that is usually found by a point of reference; e.g., a DNA sequence that is a gene, or part of a gene or intergenic region.

As used herein, "polymorphism" means the presence of one or more variations of a nucleic acid sequence at one or more loci in a population of at least two members. The variation can comprise but is not limited to one or more nucleotide base substitutions, the insertion of one or more nucleotides, a nucleotide sequence inversion, and/or the deletion of one or more nucleotides. Exemplary examples of polymorphisms include single nucleotide polymorphisms (SNPs), insertions or deletions in DNA sequence (Indels), simple sequence repeats of DNA sequence (SSRs), a restriction fragment length polymorphism, and a tag SNP. A genetic marker, a gene, a DNA-derived sequence, a haplotype, a RNA-derived sequence, a promoter, a 5' untranslated region of a gene, a 3' untranslated region of a gene, microRNA, siRNA, a QTL, a satellite marker, a transgene, mRNA, ds mRNA, a transcriptional profile, and a methylation event may also comprise polymorphisms. In addition, the presence, absence, or variation in copy number of the preceding may comprise a polymorphism.

As used herein, a "marker" is a detectable characteristic that can be used to discriminate between organisms. Examples of such characteristics may include genetic markers, biochemical markers, fermentation yield, fermentation efficiency, energy yield, secondary compounds, metabolites, morphological characteristics, and agronomic characteristics.

As used herein, a "marker assay" is a method for detecting a polymorphism at a particular locus using a particular method. Exemplary examples of marker assays include measurement of at least one genotypic trait such as restriction fragment length polymorphism (RFLP), single base extension, electrophoresis, sequence alignment, allelic specific oligonucleotide hybridization (ASO), random amplified polymorphic DNA (RAPD), microarray-based polymorphism detection technologies, and nucleic acid sequencing technologies.

As used herein, "genotype" means the genetic component of a phenotype that can be indirectly characterized using markers or directly characterized by nucleic acid sequencing.

As used herein, "genotyping" refers to any method whereby the specific allelic form of a given genomic polymorphism is determined. For example, a single nucleotide polymorphism (SNP) can be genotyped by determining which nucleotide is present (i.e. an A, G, T, or C). Insertion/deletions (Indels) can be genotyped by determining if the Indel is present. Indels can be genotyped by a variety of assays including but not limited to marker assays.

As used herein, the term "adjacent", when used to describe a nucleic acid molecule that hybridizes to DNA containing a polymorphism, refers to a nucleic acid that hybridizes to DNA sequences that directly abut the polymorphic nucleotide base position. For example, a nucleic acid molecule that can be used in a single base extension assay is "adjacent" to the polymorphism.

As used herein, "interrogation position" refers to a physical position on a solid support that can be queried to obtain genotyping data for one or more predetermined genomic polymorphisms.

As used herein, a nucleic acid molecule is the "complement" of another nucleic acid molecule if they exhibit complete complementarity.

As used herein, the term "single nucleotide polymorphism," also referred to by the abbreviation "SNP," constitutes a single base pair change, an insertion of one or more base pairs, or a deletion of one or more base pairs at a single site.

As used herein, the term "haplotype" means a chromosomal region within a haplotype window defined by two or more polymorphic molecular markers.

As used herein, the term "haplotype window" means a chromosomal region that is established by statistical analyses known to those of skill in the art and is in linkage disequilibrium. Thus, identity by state between two inbred individuals (or two gametes) at one or more molecular marker loci located within this region is taken as evidence of identity-by-descent of the entire region.

As used herein, "phenotype" means the detectable characteristics of a cell or organism which can be influenced by genotype.

As used herein, "linkage" refers to relative frequency at which types of gametes are produced in a cross. For example, if locus A has genes "A" or "a" and locus B has genes "B" or "b" and a cross between parent I with AABB and parent B with aabb will produce four possible gametes where the genes are segregated into AB, Ab, aB and ab. The null expectation is that there will be independent equal segregation into each of the four possible genotypes, i.e. with no linkage ¼ of the gametes will of each genotype. Segregation of gametes into genotypes differing from ¼ are attributed to linkage.

As used herein, "linkage disequilibrium" is defined in the context of the relative frequency of gamete types in a population of many individuals in a single generation. If the frequency of allele A is p, a is p', B is q and b is q', then the expected frequency (with no linkage disequilibrium) of genotype AB is pq, Ab is pq', aB is p'q and ab is p'q'. Any deviation from the expected frequency is called linkage disequilibrium. Two loci are considered "genetically linked" when they are in linkage disequilibrium.

As used herein, "quantitative trait locus (QTL)" means a locus that controls to some degree numerically representable traits that are usually continuously distributed.

As used herein, the term "soybean" means *Glycine max* and includes all plant varieties that can be bred with soybean, including wild soybean species.

As used herein, the term "elite line" means any line that has resulted from breeding and selection for superior agronomic performance. Exemplary examples of elite soybean varieties that are commercially available to farmers or soybean breeders include AG00802, A0868, AG0902, A1923, AG2403, A2824, A3704, A4324, A5404, AG5903 and AG6202 (Asgrow Seeds, Des Moines, Iowa, USA); BPRO144RR, BPR 4077NRR and BPR 4390NRR (Bio Plant Research, Camp Point, Ill., USA); DKB17-51 and DKB37-51 (DeKalb Genetics, DeKalb, Ill., USA); and DP 4546 RR, and DP 7870 RR (Delta & Pine Land Company, Lubbock, Tex., USA); JG 03R501, JG 32R606C ADD and JG 55R503C (JGL Inc., Greencastle, Ind., USA); NKS13-K2 (NK Division of Syngenta Seeds, Golden Valley, Minn., USA); 90M01, 91M30, 92M33, 93M11, 94M30, 95M30 and 97B52 (Pioneer Hi-Bred International, Johnston, Iowa, USA); SG4771NRR and SG5161NRR/STS (Soygenetics, LLC, Lafayette, Ind., USA); S00-K5, S11-L2, S28-Y2, S43-B1, S53-A1, S76-L9 and S78-G6 (Syngenta Seeds, Henderson, Ky., USA). An elite plant is a representative plant from an elite variety.

II. DESCRIPTION OF THE INVENTION: OVERVIEW

The present invention is an improvement over current methods of selecting soybean plants and seeds based on phenotypic characteristics because it provides methods to verify the accuracy of visual observations, such as field observations, that can be compromised by uncontrollable environmental conditions, human error, etc. In breeding operations, many resources may be wasted by investing in lines prior to discovering that the lines segregate for a desirable seed lot purity trait.

The present invention is drawn to molecular markers to select for genetic loci associated seed lot purity traits. These genetic loci are: (i) the W1 locus containing the flavonoid 3'5' hydroxylase gene at linkage group F (chromosome 13); (ii) the T locus containing the flavonoid 3' hydroxylase gene at linkage group C2 (chromosome 6); (iii) the Td locus at linkage group N (chromosome 3); (iv) the R locus at linkage group K (chromosome 9); (v) the I locus at linkage group A2 (chromosome 8); and (vi) the L2 locus linkage group N (chromosome 3).

TABLE 1

Markers spanning genomic regions associated with seed lot purity traits.

| Locus Name | Linkage Group (LG) (Chromosome) | Marker Name | Map Positions[1] | SEQ ID NO: | Allelic form(s) Associated with Seed Lot Purity Trait[2] |
|---|---|---|---|---|---|
| W1 Locus | LG F (13) | W1 allele | 4552570-4557280 | 1 | DD |
|  |  | w1 allele |  | 2 | II |
| T Locus | LG C2 (6) | M0243191[3] | 18534618-18541507 | 8 | CC or TT |
| Td Locus | LG N (3) |  | 5644434-5647952 | 13 | II |
|  |  |  |  | 14 | DD |
|  |  | M006200746[8] | 47152562-47152863 | 53 | TT or GG |
|  |  | M006200926[9] | 47212539-47212840 | 54 | TT or CC |
| R Locus | LG K (9) | M0100925[4] | 42903750-42905044 | 19 | AA or TT |
|  |  | M006934394[19] | 42526481-42526782 | 58 | AA or TT |
|  |  | M006934399[20] | 42533183-42533484 | 59 | AA or GG |
|  |  | M006934436[21] | 42543758-42544059 | 60 | AA or TT |
|  |  | M006934505[22] | 42563593-42563894 | 61 | TT or CC |
|  |  | M006934661[23] | 42625198-42625499 | 62 | AA or CC |
| I Locus | LG A2 (8) | M006725263[16] | 8356339-8356640 | 55 | TT or CC |
|  |  | M006725275[17] | 8367092-8367393 | 56 | TT or CC |
|  |  | M006725283[18] | 8372397-8372698 | 57 | TT or CC |
| L2 Locus | LG N (3) | M0202726[5] | 583905-584201 | 26 | AA or TT |
|  |  | M0119618[6] | 785516-786002 | 33 | AA or TT |
|  |  | M0094170[7] | 950081-950475 | 40 | AA or GG |
|  |  | M006065284[10] | 777977-778278 | 47 | TT or AA |
|  |  | M006065312[11] | 789372-789673 | 48 | AA or TT |
|  |  | M006065346[12] | 799426-799727 | 49 | CC or AA |
|  |  | M006065360[13] | 816587-816888 | 50 | TT or GG |
|  |  | M006065367[14] | 821682-821983 | 51 | TT or CC |
|  |  | M006065379[15] | 829690-829991 | 52 | GG or AA |

[1] The nucleotide positions of loci and markers is based on nucleotide positions of a physical map of soybean physical map of the linkage groups listed in column 2 of Table 1 (as described on the World Wide Web at soybase.org) and of Table 14 (Appendix to the Specification). Polymorphic nucleotide bases are designated in the sequence listing provided herewith according to the WIPO Standard ST.25 (1998), Table 1, as follows: r = g or a (purine); y = t/u or c (pyrimidine); m = a or c; (amino); k = g or t/u (keto); s = g or c (strong interactions 3 H-bonds); w = a or t/u (weak interactions 2H-bonds); b = g or c or t/u (not a); d = a or g or t/u (not c); h = a or c or t/u (not g); v = a or g or c (not t, not u); and n = a or g or c or t/u (unknown, or other; any.)
[2] Both the maternal and paternal alleles of the single nucleotide polymorphisms that can be associated with a seed lot purity trait are shown.
[3] The identified polymorphic allele of marker M0243191 is located at nucleotide 96 of SEQ ID NO: 8.
[4] The identified polymorphic allele of marker M0100925 is located at nucleotide 137 of SEQ ID NO: 19.
[5] The identified polymorphic allele of marker M0202726 is located at nucleotide 137 of SEQ ID NO: 26.
[6] The identified polymorphic allele of marker M0119618 is located at nucleotide 48 of SEQ ID NO: 33.
[7] The identified polymorphic allele of marker M0094170 is located at nucleotide 348 of SEQ ID NO: 40.
[8] The identified polymorphic allele of marker M006200746 is located at nucleotide 201 of SEQ ID NO: 53.
[9] The identified polymorphic allele of marker M006200926 is located at nucleotide 201 of SEQ ID NO: 54.
[10] The identified polymorphic allele of marker M006065284 is located at nucleotide 201 of SEQ ID NO: 47.
[11] The identified polymorphic allele of marker M006065312 is located at nucleotide 201 of SEQ ID NO: 48.
[12] The identified polymorphic allele of marker M006065346 is located at nucleotide 201 of SEQ ID NO: 49.
[13] The identified polymorphic allele of marker M006065360 is located at nucleotide 201 of SEQ ID NO: 50.
[14] The identified polymorphic allele of marker M006065367 is located at nucleotide 201 of SEQ ID NO: 51.
[15] The identified polymorphic allele of marker M006065379 is located at nucleotide 201 of SEQ ID NO: 52.
[16] The identified polymorphic allele of marker M006725263 is located at nucleotide 201 of SEQ ID NO: 55.
[17] The identified polymorphic allele of marker M006725275 is located at nucleotide 201 of SEQ ID NO: 56.
[18] The identified polymorphic allele of marker M006725283 is located at nucleotide 201 of SEQ ID NO: 57.
[19] The identified polymorphic allele of marker M006934394 is located at nucleotide 201 of SEQ ID NO: 58.
[20] The identified polymorphic allele of marker M006934399 is located at nucleotide 201 of SEQ ID NO: 59.
[21] The identified polymorphic allele of marker M006934436 is located at nucleotide 201 of SEQ ID NO: 60.
[22] The identified polymorphic allele of marker M006934505 is located at nucleotide 201 of SEQ ID NO: 61.
[23] The identified polymorphic allele of marker M006934661 is located at nucleotide 201 of SEQ ID NO: 62.

SNP markers were discovered in or proximal to genes in soybean that determine flower color (W1 locus), pubescence color (T and Td loci), hilum color (R locus and I locus), and pod wall color (L2 locus). These molecular markers can be used in several stages of the breeding process to make breeding more efficient and more accurate. Illustrative examples of how such molecular markers can be used in the breeding process include distinguishing true hybridization events from self-pollinations and to separate plants that are fixed for the seed lot purity traits from those that are segregating. These molecular markers may be used in soybean breeding programs to increase the purity of seeds lots for commercialization.

III. GENOTYPES ASSOCIATED WITH PHENOTYPES (i): W1 Locus—Flower color

The gene flavonoid 3'5' hydroxylase controls flower pigmentation and is located within the W1 locus of linkage group F (chromosome 13). The two variant alleles of this gene were previously cloned and sequenced (Zabala & Vodkin, Crop Sci. 47(S2): S113-S124 (2007)). A sequence alignment of the two variant alleles illustrates a 53 base pair nucleotide insertion and a 10 base pair nucleotide substitution in the w1 allele relative to the W1 allele. The 53 nucleotide insertion occurs at nucleotide base position 4237 of the W1 allele followed by a substitution of 10 nucleotides (SEQ ID: 3) creating the w1 allele. For example, primers (SEQ ID: 4 and 5) and probes (SEQ ID: 6 and 7) were designed to distinguish the variant alleles (W1 and w1) of flavonoid 3'5' hydroxylase and thus could be used, for example, to identify, select, introgress, obtain, or produce lines differing in flower color phenotype. It is understood that other primers and probes may be developed to distinguish the variant alleles W1 and w1 and to determine the allelic state of a soybean plant with respect to a genotype associated with flower color phenotype. Detection of a "deletion" genotype, "DD" (W1 allele-SEQ ID: 1), corresponds to purple flower color and the detection of an "insertion/substitution" genotype, "II" (w1 allele-SEQ ID: 2), corresponds to white flower color. The data is presented in Table 2 and shows an exact correlation between the genotype and flower color phenotype.

TABLE 2

Soybean lines Genotyped at the W1 Locus for Flower Color.

| Soybean Line | Flower Phenotype | Allelic Forms Associated with Flower Color W1 ("DD" - SEQ ID NO: 1) and w1 ("II" - SEQ IS NO: 2) |
|---|---|---|
| AG0801 | Purple | DD |
| AG0808 | White | II |
| DKB10-52 | White | II |
| AG1102 | Purple | DD |
| AG2605 | White | II |
| AG2606 | Purple | DD |
| AG2909 | White | II |
| AG3505 | Purple | DD |
| DKB35-52 | White | II |
| AG4403 | Purple | DD |
| DKB46-51 | White | II |
| AG5301 | White | II |
| AG5501 | Purple | DD |
| AG6702 | Purple | DD |
| AG7201 | White | II |

(ii) and (iii): T and Td Loci—Pubescence Color

Soybean pubescence color is controlled through the association of two loci, the T locus and the Td locus. All soybean plants have "hair" growing on the stem and leaves. This "hair" is referred to as pubescence, which expresses a definite color. Most soybean plants have either gray, tawny or light tawny colored pubescence.

The T locus is located on linkage group C2 (chromosome 6) and contains the flavonoid 3' hydroxylase gene. Within the gene is a molecular marker, M0243191 (SEQ ID:8), which distinguishes tawny or light tawny pubescence color from a gray pubescence color. The identified polymorphic allele of marker M00243191 "CC" genotype can be associated with a tawny or light tawny pubescence color and a "TT" genotype can be associated with a gray pubescence color.

The molecular marker associated with the T locus—M0243191 (SEQ ID: 8)—can be amplified, for example, using the primers indicated as SEQ ID NO: 9 and 10 and detected with probes indicated as SEQ ID NO: 11 and 12. It is understood that other primers and probes may be developed to determine the allelic state of this molecular marker and to, for example, identify, select, introgress, obtain, or produce a soybean plant with respect to a genotype associated with a certain pubescence color phenotype.

The Td locus is located on linkage group is on linkage group N (chromosome 3) and is represented by SEQ ID: 13. The Td locus nucleotide sequence with the 12 base pair deletion is represented by SEQ ID: 14 and can distinguish a light tawny pubescence color (deletion genotype "DD"), from gray and tawny pubescence color (insertion genotype, "II"). The 12 base pair nucleotide deletion occurs at nucleotide base position 300 of SEQ ID: 13.

In Table 3, 42 soybean lines were tested at the T and Td locus for pubescence color. In all tested soybean lines the T locus M0243191 marker, (SEQ ID: 8), distinguished tawny or light tawny pubescence color from a gray pubescence color. At the Td locus, the presence or absence of the 12 base pair deletion showed a near-perfect correlation between pubescence color genotypes and phenotypes. The presence or absence of the 12 base pair deletion can be amplified, for example, using the primers indicated as SEQ ID NO: 15 and SEQ ID NO: 16 and detected with probes indicated as SEQ ID NO: 17 and SEQ ID NO: 18. It is understood that other primers and probes may be developed to detect the presence or absence of this deletion and to determine the allelic variants of this marker to, for example, identify, select, introgress, obtain, or produce a soybean plant with respect to a genotype associated with a certain pubescence color phenotype.

TABLE 3

Soybean Lines Tested for Pubescence Color at the T and Td Loci.

| Soybean Line | Pubescence Color Phenotype | Allelic Form of Marker Associated with T Loci (SEQ ID: 8) | Allelic Form Associated with Td Loci (SEQ ID: 13 "II" and SEQ ID NO: 14 "DD") |
|---|---|---|---|
| 98820-33 | Light tawny | CC | DD |
| A3525 | Gray | TT | II |
| AG0801 | Tawny | CC | II |
| AG0808 | Tawny | CC | II |
| AG1102 | Tawny | CC | II |
| AG1702 | Light Tawny | CC | DD |
| AG2106 | Light tawny | CC | DD |
| AG2107 | Gray | TT | II |
| AG2110 | Gray | TT | DD |
| AG2204 | Light tawny | CC | DD |
| AG2406 | Tawny | CC | II |
| AG2605 | Light tawny | CC | DD |
| AG2606 | Light tawny | CC | DD |
| AG2802 | Gray | TT | II |
| AG2909 | Gray | TT | DD |
| AG3101 | Gray | TT | II |
| AG3205 | Gray | TT | II |
| AG3402 | Tawny | CC | II |
| AG3505 | Gray | TT | II |
| AG3705 | Tawny | CC | II |
| AG4005 | Tawny | CC | II |
| AG4303 | Light tawny | CC | DD |
| AG4403 | Light tawny | CC | DD |
| AG4801 | Tawny | CC | II |
| AG4903 | Light tawny | CC | DD |
| AG4907 | Light tawny | CC | DD |
| AG5301 | Gray | TT | II |
| AG5501 | Gray | TT | II |
| AG5606 | Tawny | CC | II |
| AG5803 | Gray | TT | II |
| AG6702 | Tawny | CC | II |
| AG7201 | Tawny | CC | II |
| AG7501 | Gray | TT | II |
| AG7502 | Tawny | CC | II |
| CST353 | Light tawny | CC | DD |
| CSTX365N | Light tawny | CC | DD |
| Dennison | Light tawny | CC | DD |
| DKB10-52 | Light tawny | CC | DD |
| DKB24-52 | Light tawny | CC | DD |
| DKB35-52 | Light tawny | CC | DD |
| DKB38-52 | Gray | TT | II |
| DKB46-51 | Tawny | CC | II |

In another study, 772 soybean lines were evaluated at the T and Td locus for pubescence color. In all tested soybean lines in Table 15, the haplotype at the Td locus on linkage group is on linkage group N (chromosome 3) containing molecular markers M006200746 (SEQ ID NO: 53) and M006200926 (SEQ ID NO: 54), distinguished tawny or light tawny pubescence color from a gray pubescence color. At the Td locus, the presence or absence of the "TT TT"

haplotype demonstrated a correlation between pubescence color genotypes and phenotypes for light tawny and tawny.

TABLE 15

Soybean Lines Genotyped at the Td locus for Pubescence Color where the allelic state of the molecular marker represented by SEQ ID NO: 8 is CC.

| Haplotype | Pubescence Color Phenotype | M006200746 (SEQ ID NO: 53) | M006200926 (SEQ ID NO: 54) | Number of Soybean Lines |
|---|---|---|---|---|
| 1 | Light Tawny | TT | TT | 228 |
| 2 | Tawny | GG | TT | 87 |
| 3 | | TT | CC | |

(iv): R Locus—Hilum Color.

The soybean seed hilum or eye is the point of attachment of the seed to the pod. Soybeans can be identified by the various hilum colors they express. Hilum colors include Black (Bl), Brown (Br), Yellow (Y), Imperfect Black (Ib), Slate (Sl), Tan (Tn), Buff (Bf) and Gray (G). The R locus is located on linkage group K (chromosome 9). A molecular marker (M0100925-SEQ ID NO: 19) was identified that co-segregates with variability at the R locus The genotypic variation of the polymorphic molecular marker was tested among 177 soybean lines segregating for hilum color and the data is presented in Table 4.

TABLE 4

Genotypic Variation Co-Segregates With Variation In Hilum Color.

| Hilum Color | Genotype at M0100925 (SEQ ID NO: 19) = "AA" | Genotype at M0100925 (SEQ ID NO: 19) = "TT" |
|---|---|---|
| Brown | 1 | 10 |
| Black | 83 | 1 |
| Imperfect black | 60 | 0 |
| Yellow | 0 | 1 |
| Buff | 18 | 3 |

As shown in Table 4, the "AA" genotype is associated with black, imperfect black, and buff hila colors, and is linked to the R allele of the R locus. The "TT" genotype is associated with brown, yellow, and buff hila colors, and is linked to the r allele for the R locus, which has been demonstrated to influence these hila colors. Buff hila color can result from the presence or either the R or r allele, although more buff lines appear to possess the R allele.

The molecular marker associated with the R locus (M0100925-SEQ ID NO: 19) can be amplified, for example, using the primers indicated as SEQ ID NO: 22 and 23 and detected with probes indicated as SEQ ID NO: 24 and 25. It is understood that other primers and probes may be developed to determine the allelic state of this molecular marker and to, for example, identify, select, introgress, obtain, or produce a soybean plant with respect to a genotype associated with a certain hilum color phenotype.

In another marker-trait association study, genotypic variation among 211 soybean lines segregating for hilum color identified molecular markers at the R locus (linkage group K-chromosome 9) (SEQ ID NO: 55-57) and the I locus (linkage group A2-chromosome 8) (SEQ ID NO: 58-62). The preferred haplotypes for hilum color identification (BL, IB, BF, BR) are shown in Table 16. The results also show the interaction of other genes controlling hilum color in soybean seed: pubescence color (T, t), flower color, (W1, w1) (Fehr, W. R., 1978. Breeding. In: A. G. Norman (Ed.), Soybean, Physiology, Agronomy and Utilization, pp. 119-155. Academic Press, New York.).

TABLE 16

The relationship of haplotypes for the molecular markers SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62 to hilum color. (The genotypes associated with pubescence color and flower color are described elsewhere herein).

| Haplotype | Hilum Color | SEQ ID NO: 55 | SEQ ID NO: 56 | SEQ ID NO: 57 | SEQ ID NO: 58 | SEQ ID NO: 59 | SEQ ID NO: 60 | SEQ ID NO: 61 | SEQ ID NO: 62 | Pubescence color | Flower Color | Number of Soybean Lines |
|---|---|---|---|---|---|---|---|---|---|---|---|---|
| 1 | BL | CC | TT | TT | AA | GG | AA | TT | AA | Tawny | White | 68 |
| 2 | | CC | TT | TT | AA | GG | AA | TT | AA | Light Tawny | Purple | |
| 3 | IB | CC | TT | TT | AA | GG | AA | TT | AA | Gray | Purple | 110 |
| 4 | BF | CC | TT | TT | AA | GG | AA | TT | AA | Gray | White | 19 |
| 5 | | CC | TT | TT | TT | AA | TT | CC | CC | Gray | Purple | |
| 6 | BR | CC | TT | TT | TT | AA | TT | CC | CC | Light Tawny | Purple | 14 |
| 7 | | CC | TT | TT | TT | AA | TT | CC | CC | Tawny | White | |

(vi): L2 Locus—Pod Wall Color.

A marker-association study for the L2 locus for pod wall color consisted of a set of 2371 lines that had information for pod wall color and genotypes on linkage group N (chromosome 3). An analysis of variance indicated that three markers, M0202726 (SEQ ID NO: 26), M0119618 (SEQ ID: 33), and M0094170 (SEQ ID: 40), were significantly associated with pod wall color (P<0.0001). When the three molecular markers were combined into a haplotype, certain haplotypes were significantly associated with tan pod walls, and others were significantly associated with brown pod walls. This is illustrated in Table 5.

TABLE 5

Molecular marker haplotypes M0202726 (SEQ ID: 26)/ M0119618 (SEQ ID: 33)/ M0094170 (SEQ ID: 40) for pod wall color.

| Haplotype defined by: M0202726 (SEQ ID NO: 26)/ M0119618 (SEQ ID NO: 33)/ M0094170 (SEQ ID NO: 40) | 1. Number of Soybean Lines | 2. Scores (Closer to 1.0 indicates tan pod wall color, closer to 3.0 indicates brown pod wall color) |
|---|---|---|
| AA GG AA | 1324 | 1.2 |
| AA GG GG | 87 | 1.1 |
| AA GT AG | 37 | 1.6 |

TABLE 5-continued

Molecular marker haplotypes M0202726 (SEQ ID: 26)/
M0119618 (SEQ ID: 33)/
M0094170 (SEQ ID: 40) for pod wall color.

| Haplotype defined by:<br>M0202726 (SEQ ID NO: 26)/<br>M0119618 (SEQ ID NO: 33)/<br>M0094170 (SEQ ID NO: 40) | 1. Number of Soybean Lines | 2. Scores (Closer to 1.0 indicates tan pod wall color, closer to 3.0 indicates brown pod wall color) |
|---|---|---|
| AA GT GG | 21 | 1.3 |
| AA TT AA | 39 | 1.6 |

TABLE 5-continued

Molecular marker haplotypes M0202726 (SEQ ID: 26)/
M0119618 (SEQ ID: 33)/
M0094170 (SEQ ID: 40) for pod wall color.

| Haplotype defined by:<br>M0202726 (SEQ ID NO: 26)/<br>M0119618 (SEQ ID NO: 33)/<br>M0094170 (SEQ ID NO: 40) | 1. Number of Soybean Lines | 2. Scores (Closer to 1.0 indicates tan pod wall color, closer to 3.0 indicates brown pod wall color) |
|---|---|---|
| AA TT GG | 573 | 2.2 |
| TT GG AA | 25 | 2.6 |
| TT TT AA | 171 | 2.9 |
| TT TT GG | 94 | 2.7 |

In Table 5, the first two and last two haplotypes are associated with tan and brown pod wall color. Several haplotypes are not clearly associated with one category. The haplotype (AA TT GG) has a score of 2.2, which indicates that it is slightly more predictive of brown pod walls, but the haplotype has almost as many soybean lines with tan pod walls.

The molecular marker M0202726 (SEQ ID: 26) can be amplified, for example, using the primers indicated as SEQ ID NO: 29 and 30 and detected with probes indicated as SEQ ID NO: 31 and 32. The molecular marker M0119618 (SEQ ID: 33) can be amplified, for example, using the primers indicated as SEQ ID NO: 36 and 37 and detected with probes indicated as SEQ ID NO: 38 and 39. The molecular M0094170 (SEQ ID: 40) can be amplified, for example, using the primers indicated as SEQ ID NO: 43 and 44 and detected with probes indicated as SEQ ID NO: 45 and 46. It is understood that other primers and probes may be developed to determine the allelic state of the molecular markers comprising this haplotype and to, for example, identify, select, introgress, obtain, or produce a soybean plant with respect to a genotype associated with a certain pod wall color phenotype.

A second marker-trait association study was conducted on the L2 locus for pod wall color on a set of 308 soybean lines. An analysis of variance indicated that six molecular markers, SEQ ID NO: 47, SEQ ID NO: 48, SEQ ID NO: 49, SEQ ID NO: 50, SEQ ID NO: 51, and SEQ ID NO: 52, were highly significantly associated with pod wall color ($P<0.001$). When the three markers were combined into a haplotype, a distinct haplotype were associated with brown pod walls and another haplotype was associated with tan pod walls (Table 17).

TABLE 17

The relationship of haplotypes for the molecular markers SEQ ID NO: 47, SEQ ID NO: 48, SEQ ID NO: 49, SEQ ID NO: 50, SEQ ID NO: 51, and SEQ ID NO: 52 to pod wall color.

| Haplotype | Pod Wall Color | Haplotype | | | | | | Number of Soybean Lines Evaluated |
|---|---|---|---|---|---|---|---|---|
| | | SEQ ID NO: 47 | SEQ ID NO: 48 | SEQ ID NO: 49 | SEQ ID NO: 50 | SEQ ID NO: 51 | SEQ ID NO: 52 | |
| 1 | BR | TT | AA | CC | TT | TT | GG | 190 |
| 2 | TN | AA | TT | AA | GG | CC | AA | 118 |

Haplotype 1 is with brown pod wall color. Haplotype 2 is associated with tan wall color.

IV

The present invention further provides that a soybean plant is selected from the group consisting of members of the genus *Glycine*, more specifically from the group consisting of *Glycine arenaria*, *Glycine argyrea*, *Glycine canescens*, *Glycine clandestine*, *Glycine curvata*, *Glycine cyrtoloba*, *Glycine falcate*, *Glycine latifolia*, *Glycine latrobeana*, *Glycine max*, *Glycine microphylla*, *Glycine pescadrensis*, *Glycine pindanica*, *Glycine rubiginosa*, *Glycine soja*, *Glycine* sp., *Glycine stenophita*, *Glycine tabacina* and *Glycine tomentella*.

It is further understood that a soybean plant of the present invention may exhibit the characteristics of any relative maturity group: 000, 00, 0, 1, 2, 3, 4, 5, 6, 7, 8, 9, and 10. An allele of a QTL can comprise multiple genes or other genetic factors even within a contiguous genomic region or linkage group, such as a haplotype. As used herein, an allele of a QTL can therefore encompass more than one gene or other genetic factor where each individual gene or genetic component is also capable of exhibiting allelic variation and where each gene or genetic factor is also capable of eliciting a phenotypic effect on the quantitative trait in question. In one aspect of the present invention the allele of a QTL comprises one or more genes or other genetic factors that are also capable of exhibiting allelic variation. The use of the term "an allele of a QTL" is thus not intended to exclude a QTL that comprises more than one gene or other genetic factor. Specifically, an "allele of a QTL" in the present invention can denote a haplotype within a haplotype window. A haplotype window is a contiguous genomic region that can be defined, and tracked, with a set of one or more polymorphic markers wherein the polymorphisms indicate identity by descent. A haplotype within that window can be defined by the unique fingerprint of alleles at each marker.

The present invention also provides for parts of the plants of the present invention. Exemplary plant parts include seed, endosperm, ovule, and pollen. Plants or parts thereof of the present invention may be grown in culture and regenerated. Methods for the regeneration of *Glycine max* plants from various tissue types and methods for the tissue culture of *Glycine max* are known in the art (See, for example, Widholm et al., *In Vitro Selection and Culture-induced Variation in Soybean*, In Soybean: Genetics, Molecular Biology and Biotechnology, Eds. Verma and Shoemaker, CAB International, Wallingford, Oxon, England (1996). Regeneration techniques for plants such as *Glycine max* can use as the starting material a variety of tissue or cell types. With *Glycine max* in particular, regeneration processes have been developed that begin with certain differentiated tissue types such as meristems, Cartha et al., *Can. J. Bot.* 59:1671-1679 (1981), hypocotyl sections, Cameya et al., *Plant Science Letters* 21: 289-294 (1981), and stem node segments, Saka et al., *Plant Science Letters*, 19: 193-201 (1980); Cheng et al., *Plant Science Letters*, 19: 91-99 (1980). Regeneration of whole sexually mature *Glycine max* plants from somatic embryos generated from explants of immature *Glycine max* embryos has been reported (Ranch et al., *In Vitro Cellular & Developmental Biology* 21: 653-658 (1985). Regeneration of mature *Glycine max* plants from tissue culture by organogenesis and embryogenesis has also been reported (Barwale et al., *Planta* 167: 473-481 (1986); Wright et al., *Plant Cell Reports* 5: 150-154 (1986).

In certain embodiments of the invention, a method of selecting for varietal purity in a soybean line, such as for a seed lot, comprises (A) crossing at least one first soybean plant comprising a nucleic acid molecule selected from the group consisting of SEQ ID NO: 1, 2, 8, 13-14, 19, 26, 33, and 40 with at least one second soybean plant in order to form a population, (B) screening the population with one or more nucleic acid markers to determine if one or more soybean plants from the population contains the nucleic acid molecule, and (C) selecting from the population one or more soybean plants comprising a nucleic acid molecule selected from the group consisting of SEQ ID NO: 1, 2, 8, 13-14, 19, 26, 33, and 40.

The present invention also includes a method of introgressing an allele into a soybean plant comprising: (A) crossing at least two soybean plants in order to form a population; (B) screening the population with one or more nucleic acid markers to determine at least one allele at one or more of the loci W1, T, Td, R, I, or L2 of one or more soybean plants from the population and (C) bulk individuals from the population with similar alleles of at least one of the W1, T, Td, R, I, or L2 loci.

The present invention includes isolated nucleic acid molecules. Such molecules include those nucleic acid molecules capable of detecting a polymorphism genetically or physically linked to the W1, T, Td, R, I, or L2 loci. Such nucleic acid molecules capable of detecting a polymorphism genetically or physically linked to the W1, T, Td, R, I, or L2 loci include SEQ ID NO: 1 through SEQ ID NO: 46, fragments thereof, complements thereof, and nucleic acid molecules capable of specifically hybridizing to one or more of these nucleic acid molecules.

In certain embodiments of the invention, a nucleic acid molecule of the present invention includes those that will specifically hybridize to one or more of the nucleic acid molecules set forth in SEQ ID NO: 1 through 46 or complements thereof or fragments of either under moderately stringent conditions, for example at about 2.0×SSC and about 65° C. In certain embodiments of the invention, a nucleic acid of the present invention will specifically hybridize to one or more of the nucleic acid molecules set forth in SEQ ID NO: 1 through 46 or complements or fragments of either under high stringency conditions. In certain embodiments of the invention, a marker nucleic acid molecule of the present invention comprises the nucleic acid sequence set forth in SEQ ID NO: 1 through 34 or complements thereof or fragments of either. In certain embodiments of the invention, a marker nucleic acid molecule of the present invention shares between 80% and 100% or 90% and 100% sequence identity with the nucleic acid sequences set forth in SEQ ID NO: 1 through 46 or complements thereof or fragments of either. In certain embodiments of the invention, a marker nucleic acid molecule of the present invention shares between 95% and 100% sequence identity with the sequences set forth in SEQ ID NO: 1 through 46 or complements thereof or fragments of either. In certain embodiments of the present invention, a marker nucleic acid molecule of the present invention shares between 98% and 100% sequence identity with the nucleic acid sequence set forth in SEQ ID NO: 1 through 46 or complement thereof or fragments of either.

V. MOLECULAR ASSISTED BREEDING TECHNIQUES

Genetic markers that can be used in the practice of the instant invention include, but are not limited to, are Restriction Fragment Length Polymorphisms (RFLP), Amplified Fragment Length Polymorphisms (AFLP), Simple Sequence Repeats (SSR), Single Nucleotide Polymorphisms (SNP), Insertion/Deletion Polymorphisms (Indels), Variable Number Tandem Repeats (VNTR), and Random Amplified Polymorphic DNA (RAPD), and others known to those skilled in the art. Marker discovery and development in crops provides the initial framework for applications to marker-assisted breeding activities (US Patent Applications 2005/0204780, 2005/0216545, 2005/0218305, and 2006/00504538). The resulting "genetic map" is the representation of the relative position of characterized loci (DNA markers or any other locus for which alleles can be identified) along the chromosomes. The measure of distance on this map is relative to the frequency of crossover events between sister chromatids at meiosis.

As a set, polymorphic markers serve as a useful tool for fingerprinting plants to inform the degree of identity of lines or varieties (U.S. Pat. No. 6,207,367). These markers form the basis for determining associations with phenotype and can be used to drive genetic gain. The implementation of marker-assisted selection is dependent on the ability to detect underlying genetic differences between individuals.

Certain genetic markers for use in the present invention include "dominant" or "codominant" markers. "Codominant markers" reveal the presence of two or more alleles (two per diploid individual). "Dominant markers" reveal the presence of only a single allele. The presence of the dominant marker phenotype (e.g., a band of DNA) is an indication that one allele is present in either the homozygous or heterozygous condition. The absence of the dominant marker phenotype (e.g., absence of a DNA band) is merely evidence that "some other" undefined allele is present. In the case of populations where individuals are predominantly homozygous and loci are predominantly dimorphic, dominant and codominant markers can be equally valuable. As populations become more heterozygous and multiallelic, codominant markers often become more informative of the genotype than dominant markers.

In another embodiment, markers that include. but are not limited, to single sequence repeat markers (SSR), AFLP markers, RFLP markers, RAPD markers, phenotypic markers, isozyme markers, single nucleotide polymorphisms (SNPs), insertions or deletions (Indels), single feature polymorphisms (SFPs, for example, as described in Borevitz et al. 2003 Gen. Res. 13:513-523), microarray transcription profiles, DNA-derived sequences, and RNA-derived sequences that are genetically linked to or correlated with seed purity, regions flanking seed purity loci, regions linked to seed purity, and/or regions that are unlinked to seed purity can be used in certain embodiments of the instant invention In one embodiment, nucleic acid-based analyses for determining the presence or absence of the genetic polymorphism (i.e. for genotyping) can be used for the selection of seeds in a breeding population. A wide variety of genetic markers for the analysis of genetic polymorphisms are available and known to those of skill in the art. The analysis may be used to select for genes, portions of genes, QTL, alleles, or genomic regions (Genotypes) that comprise or are linked to a genetic marker that is linked to or correlated with seed purity, regions flanking seed purity loci, regions linked to seed purity, and/or regions that are unlinked to seed purity can be used in certain embodiments of the instant invention.

Herein, nucleic acid analysis methods include, but are not limited to, PCR-based detection methods (for example, TaqMan assays), microarray methods, mass spectrometry-based methods and/or nucleic acid sequencing methods. In one embodiment, the detection of polymorphic sites in a sample of DNA, RNA, or cDNA may be facilitated through the use of nucleic acid amplification methods. Such methods specifically increase the concentration of polynucleotides that span the polymorphic site, or include that site and sequences located either distal or proximal to it. Such amplified molecules can be readily detected by gel electrophoresis, fluorescence detection methods, or other means.

A method of achieving such amplification employs the polymerase chain reaction (PCR) (Mullis et al. 1986 Cold Spring Harbor Symp. Quant. Biol. 51:263-273; European Patent 50,424; European Patent 84,796; European Patent 258,017; European Patent 237,362; European Patent 201, 184; U.S. Pat. No. 4,683,202; U.S. Pat. No. 4,582,788; and U.S. Pat. No. 4,683,194), using primer pairs that are capable of hybridizing to the proximal sequences that define a polymorphism in its double-stranded form.

Methods for typing DNA based on mass spectrometry can also be used. Such methods are disclosed in U.S. Pat. Nos. 6,613,509 and 6,503,710, and references found therein. Polymorphisms in DNA sequences can be detected or typed by a variety of effective methods well known in the art including, but not limited to, those disclosed in U.S. Pat. Nos. 5,468,613, 5,217,863; 5,210,015; 5,876,930; 6,030, 787; 6,004,744; 6,013,431; 5,595,890; 5,762,876; 5,945, 283; 5,468,613; 6,090,558; 5,800,944; 5,616,464; 7,312, 039; 7,238,476; 7,297,485; 7,282,355; 7,270,981 and 7,250, 252 all of which are incorporated herein by reference in their entireties. However, the compositions and methods of the present invention can be used in conjunction with any polymorphism typing method to type polymorphisms in genomic DNA samples. These genomic DNA samples used include but are not limited to genomic DNA isolated directly from a plant, cloned genomic DNA, or amplified genomic DNA.

For instance, polymorphisms in DNA sequences can be detected by hybridization to allele-specific oligonucleotide (ASO) probes as disclosed in U.S. Pat. Nos. 5,468,613 and 5,217,863. U.S. Pat. No. 5,468,613 discloses allele specific oligonucleotide hybridizations where single or multiple nucleotide variations in nucleic acid sequence can be detected in nucleic acids by a process in which the sequence containing the nucleotide variation is amplified, spotted on a membrane and treated with a labeled sequence-specific oligonucleotide probe.

Target nucleic acid sequence can also be detected by probe ligation methods as disclosed in U.S. Pat. No. 5,800, 944 where sequence of interest is amplified and hybridized to probes followed by ligation to detect a labeled part of the probe.

Microarrays can also be used for polymorphism detection, wherein oligonucleotide probe sets are assembled in an overlapping fashion to represent a single sequence such that a difference in the target sequence at one point would result in partial probe hybridization (Borevitz et al., Genome Res. 13:513-523 (2003); Cui et al., Bioinformatics 21:3852-3858 (2005). On any one microarray, it is expected there will be a plurality of target sequences, which may represent genes and/or noncoding regions wherein each target sequence is represented by a series of overlapping oligonucleotides, rather than by a single probe. This platform provides for high throughput screening a plurality of polymorphisms. A single-feature polymorphism (SFP) is a polymorphism detected by a single probe in an oligonucleotide array, wherein a feature is a probe in the array. Typing of target sequences by microarray-based methods is disclosed in U.S. Pat. Nos. 6,799,122; 6,913,879; and 6,996,476.

Target nucleic acid sequence can also be detected by probe linking methods as disclosed in U.S. Pat. No. 5,616, 464, employing at least one pair of probes having sequences homologous to adjacent portions of the target nucleic acid sequence and having side chains which non-covalently bind to form a stem upon base pairing of the probes to the target nucleic acid sequence. At least one of the side chains has a photoactivatable group which can form a covalent cross-link with the other side chain member of the stem.

Other methods for detecting SNPs and Indels include single base extension (SBE) methods. Examples of SBE methods include, but are not limited to, those disclosed in U.S. Pat. Nos. 6,004,744; 6,013,431; 5,595,890; 5,762,876; and 5,945,283. SBE methods are based on extension of a nucleotide primer that is adjacent to a polymorphism to incorporate a detectable nucleotide residue upon extension of the primer. In certain embodiments, the SBE method uses three synthetic oligonucleotides. Two of the oligonucleotides serve as PCR primers and are complementary to sequence of the locus of genomic DNA which flanks a region containing the polymorphism to be assayed. Following amplification of the region of the genome containing the polymorphism, the PCR product is mixed with the third oligonucleotide (called an extension primer) which is designed to hybridize to the amplified DNA adjacent to the polymorphism in the presence of DNA polymerase and two differentially labeled dideoxynucleosidetriphosphates.

If the polymorphism is present on the template, one of the labeled dideoxynucleosidetriphosphates can be added to the primer in a single base chain extension. The allele present is then inferred by determining which of the two differential labels was added to the extension primer. Homozygous samples will result in only one of the two labeled bases being incorporated and thus only one of the two labels will be detected. Heterozygous samples have both alleles present, and will thus direct incorporation of both labels (into different molecules of the extension primer) and thus both labels will be detected.

In another method for detecting polymorphisms, SNPs and Indels can be detected by methods disclosed in U.S. Pat. Nos. 5,210,015; 5,876,930; and 6,030,787 in which an oligonucleotide probe having a 5' fluorescent reporter dye and a 3' quencher dye covalently linked to the 5' and 3' ends of the probe. When the probe is intact, the proximity of the reporter dye to the quencher dye results in the suppression of the reporter dye fluorescence, e.g. by Forster-type energy transfer. During PCR forward and reverse primers hybridize to a specific sequence of the target DNA flanking a polymorphism while the hybridization probe hybridizes to polymorphism-containing sequence within the amplified PCR product. In the subsequent PCR cycle DNA polymerase with 5'→3' exonuclease activity cleaves the probe and separates the reporter dye from the quencher dye resulting in increased fluorescence of the reporter.

In another embodiment, the locus or loci of interest can be directly sequenced using nucleic acid sequencing technologies. Methods for nucleic acid sequencing are known in the art and include technologies provided by 454 Life Sciences (Branford, Conn.), Agencourt Bioscience (Beverly, Mass.), Applied Biosystems (Foster City, Calif.), LI-COR Biosciences (Lincoln, Nebr.), NimbleGen Systems (Madison, Wis.), Illumina (San Diego, Calif.), and VisiGen Biotechnologies (Houston, Tex.). Such nucleic acid sequencing technologies comprise formats such as parallel bead arrays, sequencing by ligation, capillary electrophoresis, electronic microchips, "biochips," microarrays, parallel microchips, and single-molecule arrays, as reviewed by R.F. Service Science 2006 311:1544-1546.

The markers to be used in the methods of the present invention should preferably be diagnostic of origin in order for inferences to be made about subsequent populations. Experience to date suggests that SNP markers may be ideal for mapping because the likelihood that a particular SNP allele is derived from independent origins in the extant populations of a particular species is very low. As such, SNP markers appear to be useful for tracking and assisting introgression of QTLs, particularly in the case of Genotypes.

EXAMPLES

The following examples are included to demonstrate preferred embodiments of the invention. It should be appreciated by those of skill in the art that the techniques disclosed in the examples which follow represent techniques discovered by the inventor to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1. Identification of Self-Pollinating Events in an $F_1$ Generation

Two lines are used as parents ("Parent A" and "Parent B") of an $F_1$ population. The parents differ in alleles at the W, T, Td, R, and L2 loci. Molecular markers from these loci can be used to distinguish $F_1$ plants that are the result of a hybridization between the two parents (example: "$F_1$ #1") from plants that are the result of a self-pollination of Parent A (example: "$F_1$ #2") shown in Table 6.

TABLE 6

Self-pollinating events in an F1 generation.

| Line/Plant | W locus | T locus | Td locus | L2 locus | R locus | Analysis |
|---|---|---|---|---|---|---|
| Parent A | DD | CC | II | AA GG AA | TT | |
| Parent B | II | TT | DD | TT TT GG | AA | |
| $F_1$ #1 | DI | CT | DI | AT GT AG | AT | True $F_1$ |
| $F_1$ #2 | DD | CC | II | AA GG AA | TT | Self-pollination |

Example 2. Early Selection of Seed Lot Purity Traits in a Soybean Breeding Program The seed lot purity traits of flower, pubescence, hilum, and pod wall color can be fixed as early as in the F2 generation in a breeding program. A breeder can use molecular marker assays to evaluate the progeny for the W1, T, Td, L2, and R loci. The breeder can maintain soybean plants that are homozygous at the W1, T, Td, L2, and R loci and discard soybean plants that are segregating for these seed lot purity traits. (Table 7).

Two lines are used as parents ("Parent A" and "Parent B") of an $F_2$ population. A breeder can determine which plants are segregating for the traits associated with the W, T, Td, L2, and R loci to discard (e.g., "$F_2$ #1" and $F_2$ #3 in Table 7) and which plants are homozygous for the traits to keep (e.g., "$F_2$ #2" and $F_2$ #4 in Table 7).

TABLE 7

Selection of Seed Lot Purity Traits of an $F_2$ population.

| Line/Plant | W locus | T locus | Td locus | L2 locus | R locus | Analysis |
|---|---|---|---|---|---|---|
| Parent A | DD | CC | II | AA GG AA | TT | |
| Parent B | II | TT | DD | TT TT GG | AA | |
| $F_2$ #1 | DI | TT | DI | AT GT AG | TT | Discard |
| $F_2$ #2 | II | CC | II | AA GG AA | AA | Keep |
| $F_2$ #3 | DD | CC | DI | TT TT GG | AT | Discard |
| $F_2$ #4 | DD | TT | II | TT TT GG | TT | Keep |

Example 3. Validation of Phenotype in the $F_6$ Generation

The environmental conditions, for example weather, can prevent an accurate determination of seed lot purity traits of $F_{5:6}$ lines. Breeders can use molecular markers to validate their field observations or to confirm their breeder's notes as shown in Table 8.

Markers for the traits associated with the W, T, Td, L2, and R loci can be used to validate visual observations of flower color, pubescence color, pod wall color, and hilum of $F_{5:6}$ lines.

TABLE 8

Validation of Phenotype in the $F_6$ Generation

| Line | Visual Observation | Marker Data Result | Action |
|---|---|---|---|
| $F_{5:6}$ #1 | Pod wall is tan | Pod wall is mixed tan/brown | Check the line in the field again |
| $F_{5:6}$ #2 | Flower color is white | Flower color is white | Observation is validated |
| $F_{5:6}$ #3 | Pubescence is mixed light tawny/gray | Pubescence is gray | Check the line in the field again |
| $F_{5:6}$ #4 | Hilum is brown | Hilum is black | Check the seed again |

Example 4. Characterizing Flower Color Through the Use of Molecular Markers

Soybean flower color is used as a classification characteristic to differentiate and describe soybean varieties. Flower colors are typically either purple or white, although there is some variation of color in wild perennial *Glycine* species and cultivars. Visual observation has been the gold standard used to determine flower color. Environmental factors such as temperature, moisture, and nutrient availability can contribute to phenotypic variation among soybean plant varieties; which can lead to errors in determining inherited traits and soybean plant variety purity. The gene flavonoid 3'5' hydroxylase controls flower pigmentation and is located within the W1 locus of linkage group F (chromosome 13). The two variant alleles of this gene were previously cloned and sequenced (Zabala & Vodkin, *Crop Sci.* 47(S2): S113-S124 (2007)). Alignment of the two genomic sequences suggested the mutation contains an insertion of 53 extra bases and a substitution of 10 nucleotides in the w1 allele relative to the W1 allele. Using this information, primers were designed to detect the variant alleles of flavonoid 3'5' hydroxylase among 16 soybean lines differing in flower color phenotype. Detection of a deletion (DD) (W1 allele-SEQ ID: 1) corresponds to purple flower color and the detection of an insertion (II) (w1 allele-SEQ ID: 2) corresponds to white flower color. The data is presented in Table 9 and shows an exact correlation between the genotype and flower color phenotype.

TABLE 9

Soybean Lines Genotyped at the W1 Locus for Flower Color.

| Soybean Line | Flower Phenotype | Allelic Form Associated with Flower Color |
|---|---|---|
| AG0801 | Purple | DD |
| AG0808 | White | II |
| DKB10-52 | White | II |
| AG1102 | Purple | DD |
| AG2605 | White | II |
| AG2606 | Purple | DD |
| AG2909 | White | II |
| AG3505 | Purple | DD |
| DKB35-52 | White | II |
| AG4403 | Purple | DD |
| DKB46-51 | White | II |
| AG5301 | White | II |
| AG5501 | Purple | DD |
| AG6702 | Purple | DD |
| AG7201 | White | II |

Example 5. Characterizing Pubescence Color Through the Use of Molecular Markers

Soybean pubescence color is controlled through the association of two loci, the T locus and the Td locus. The T locus is located on linkage group C2 (chromosome 6) and contains the flavonoid 3' hydroxylase gene. Within the gene is a molecular marker, M0243191 (SEQ ID: 8), which distinguishes tawny or light tawny pubescence color from a gray pubescence color. The identified polymorphic allele of marker M00243191 "CC" genotype can be associated with a tawny or light tawny pubescence color and a "TT" genotype can be associated with a gray pubescence color.

The Td locus is located on linkage group is on linkage group N (chromosome 3). The detection of a 12 base pair deletion in the Td locus (see SEQ ID: 13 and SEQ ID: 14) can distinguish a light tawny pubescence color, (deletion genotype "DD"), from gray and tawny pubescence color (insertion genotype, "II").

In Table 10, 42 soybean lines were tested at the T and Td locus for pubescence color. In all tested soybean lines the T locus M0243191 marker, (SEQ ID: 8), distinguished tawny or light tawny pubescence color from a gray pubescence color. At the Td locus, the presence or absence of the 12 base pair deletion showed a near-perfect correlation between pubescence color genotypes and phenotypes.

TABLE 10

Soybean Lines Genotyped at the T and Td loci for Pubescence Color.

| Soybean Line | Pubescence Color Phenotype | Allelic Form of Marker Associated with T Loci (SEQ ID: 8) | Allelic Form Associated with Td Loci (SEQ ID: 13 and SEQ ID NO: 14) |
|---|---|---|---|
| 98820-33 | Light tawny | CC | DD |
| A3525 | Gray | TT | II |
| AG0801 | Tawny | CC | II |
| AG0808 | Tawny | CC | II |
| AG1102 | Tawny | CC | II |
| AG1702 | Light Tawny | CC | DD |
| AG2106 | Light tawny | CC | DD |
| AG2107 | Gray | TT | II |
| AG2110 | Gray | TT | DD |
| AG2204 | Light tawny | CC | DD |
| AG2406 | Tawny | CC | II |
| AG2605 | Light tawny | CC | DD |
| AG2606 | Light tawny | CC | DD |
| AG2802 | Gray | TT | II |
| AG2909 | Gray | TT | DD |
| AG3101 | Gray | TT | II |
| AG3205 | Gray | TT | II |
| AG3402 | Tawny | CC | II |
| AG3505 | Gray | TT | II |
| AG3705 | Tawny | CC | II |
| AG4005 | Tawny | CC | II |
| AG4303 | Light tawny | CC | DD |
| AG4403 | Light tawny | CC | DD |
| AG4801 | Tawny | CC | II |
| AG4903 | Light tawny | CC | DD |
| AG4907 | Light tawny | CC | DD |
| AG5301 | Gray | TT | II |
| AG5501 | Gray | TT | II |
| AG5606 | Tawny | CC | II |
| AG5803 | Gray | TT | II |
| AG6702 | Tawny | CC | II |
| AG7201 | Tawny | CC | II |
| AG7501 | Gray | TT | II |
| AG7502 | Tawny | CC | II |
| CST353 | Light tawny | CC | DD |
| CSTX365N | Light tawny | CC | DD |
| Dennison | Light tawny | CC | DD |
| DKB10-52 | Light tawny | CC | DD |

TABLE 10-continued

Soybean Lines Genotyped at the T and Td loci for Pubescence Color.

| Soybean Line | Pubescence Color Phenotype | Allelic Form of Marker Associated with T Loci (SEQ ID: 8) | Allelic Form Associated with Td Loci (SEQ ID: 13 and SEQ ID NO: 14) |
|---|---|---|---|
| DKB24-52 | Light tawny | CC | DD |
| DKB35-52 | Light tawny | CC | DD |
| DKB38-52 | Gray | TT | II |
| DKB46-51 | Tawny | CC | II |

In another study, 772 soybean line were tested at the T and Td locus for pubescence color. In all tested soybean lines in Table 18, the haplotype at the Td locus on linkage group is on linkage group N (chromosome 3) containing molecular markers M006200746 (SEQ ID NO: 53) and M006200926 (SEQ ID NO: 54), distinguished tawny or light tawny pubescence color from a gray pubescence color. At the Td locus, the presence or absence of the "TT TT" haplotype demonstrated a correlation between pubescence color genotypes and phenotypes for light tawny and tawny.

TABLE 18

Soybean Lines Genotyped at the Td locus for Pubescence Color.

| | | Haplotype | | |
|---|---|---|---|---|
| Haplotype | Pubescence Color Phenotype | M006200746 (SEQ ID NO: 53) | M006200926 (SEQ ID NO: 54) | # of Lines |
| 1 | Light Tawny | TT | TT | 228 |
| 2 | Tawny | GG | TT | 87 |
| 3 | | TT | CC | |

Example 6. Characterizing Hilum Color Through the Use of Molecular Markers

Soybean hilum color is a key classification characteristic used to describe soybean plant varieties. Hilum color can be used to identify a soybean plant variety and establish the purity of seed lots. Hilum color is classified as black, imperfect black, brown, reddish brown, gray, buff, or yellow and is determined by visual observations.

Hilum is controlled by the interaction of five genes: pubescence color (T, t), flower color, (W1, w1) and genes controlling the distribution and color of pigmentation in the seed [(I, ii), (R, r), and (O, o)]. The molecular markers associated with pubescence color and flower color were described in earlier examples within this section.

Marker-trait association studies were used to identify molecular markers that co-segregated with variation at the R locus. Genotypic variation among 177 lines segregating for hilum color was assessed in the region surrounding the R locus, which is on linkage group K (chromosome 9) of the public genomic map. The allelic variation at the marker SEQ ID NO: 19 co-segregated with differences in hilum color (Table 11).

TABLE 11

Genotypic variation at SEQ ID NO: 19 co-segregates with variation in hilum color.

| Hilum Color | Genotype at SEQ ID NO: 19 = "AA" | Genotype at SEQ ID NO: 19 = "TT" |
|---|---|---|
| Brown (BR) | 1 | 10 |
| Black (BL) | 83 | 1 |
| Imperfect black (IB) | 60 | 0 |
| Yellow (Y) | 0 | 1 |
| Buff (BF) | 18 | 3 |

The "TT" genotype is associated with brown, yellow, and buff hila colors. The "TT" genotype thus seems to be linked to the recessive r allele of the R locus, which has been demonstrated to influence these hila colors. The "AA" genotype is associated with black, imperfect black, and buff hila colors, and thus seems to be linked to the dominant R allele of the R locus. Buff hilum color can thus result from the presence of either the R or r allele, although more buff lines appear to possess the R allele. Based on flower color, pubescence color, and R locus, many of the classes of hilum color can be characterized through the use of molecular markers.

In another marker-trait association study, genotypic variation among 211 soybean lines In another marker-trait association study, genotypic variation among 211 soybean lines segregating for hilum color identified molecular markers at the R locus (linkage group K-chromosome 9) (SEQ ID NO: 55-57) and the I locus (linkage group A2-chromosome 8) (SEQ ID NO: 58-62). The preferred haplotypes for hilum color identification (BL, IB, BF, BR) are shown in Table 19. The results also show the interaction of other genes controlling hilum color in soybean seed: pubescence color (T, t), flower color, (W1, w1) (Fehr, W. R., 1978. Breeding. In: A. G. Norman (Ed.), Soybean, Physiology, Agronomy and Utilization, pp. 119-155. Academic Press, New York.).

TABLE 19

The relationship of haplotypes for the molecular markers SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62 to hilum color.

| | | Haplotype | | | | | | | | | Number of |
|---|---|---|---|---|---|---|---|---|---|---|---|
| Haplotype | Hilum Color | SEQ ID NO: 55 | SEQ ID NO: 56 | SEQ ID NO: 57 | SEQ ID NO: 58 | SEQ ID NO: 59 | SEQ ID NO: 60 | SEQ ID NO: 61 | SEQ ID NO: 62 | Pubescence color | Flower Color | Soybean Lines |
| 1 | BL | CC | TT | TT | AA | GG | AA | TT | AA | Tawny | White | 68 |
| 2 | | CC | TT | TT | AA | GG | AA | TT | AA | Light Tawny | Purple | |
| 3 | IB | CC | TT | TT | AA | GG | AA | TT | AA | Gray | Purple | 110 |
| 4 | BF | CC | TT | TT | AA | GG | AA | TT | AA | Gray | White | 19 |

TABLE 19-continued

The relationship of haplotypes for the molecular markers SEQ ID NO: 55, SEQ ID NO: 56, SEQ ID NO: 57, SEQ ID NO: 58, SEQ ID NO: 59, SEQ ID NO: 60, SEQ ID NO: 61, and SEQ ID NO: 62 to hilum color.

| Haplotype | Hilum Color | SEQ ID NO: 55 | SEQ ID NO: 56 | SEQ ID NO: 57 | SEQ ID NO: 58 | SEQ ID NO: 59 | SEQ ID NO: 60 | SEQ ID NO: 61 | SEQ ID NO: 62 | Pubescence color | Flower Color | Number of Soybean Lines |
|---|---|---|---|---|---|---|---|---|---|---|---|---|
| 5 |    | CC | TT | TT | TT | AA | TT | CC | CC | Gray | Purple |    |
| 6 | BR | CC | TT | TT | TT | AA | TT | CC | CC | Light Tawny | Purple | 14 |
| 7 |    | CC | TT | TT | TT | AA | TT | CC | CC | Tawny | White |    |

Example 7. Characterizing Pod Wall Color Through the Use of Molecular Markers

Pod wall color is a key classification characteristic used to describe soybean varieties. Pod wall color is generally classified as brown or tan. Visual observations are typically used to determine pod wall color. Approximately 5% of the selections advanced through to the first stage of elite yield testing are incorrectly identified as fixed for characteristic traits; many resources were invested in these soybean lines prior to realizing that the soybean lines were in fact segregating, often for pod wall color. Molecular marker associated with such purity marker traits will confirm or refute visual observations or discrepancies in the data.

The L2 locus is associated with pod wall color. A marker-association study was conducted on the L2 locus for pod wall color on a set of 2371 soybean lines. An analysis of variance indicated that three molecular markers, SEQ ID NO: 26, SEQ ID NO: 33, and SEQ ID NO: 40 were highly significantly associated with pod wall color (P<0.0001). Pod color type was further rated for this study: Brown (BR)=1, Mixed (MX)=2, and Tan (TN)=3. When the three markers were combined into a haplotype, distinct haplotypes were significantly associated with Brown (BR) pod walls and other haplotypes were associated with Mixed (MX) and Tan (TN) pod walls (Table 12).

TABLE 12

The relationship of haplotypes for the molecular markers SEQ ID NO: 26, SEQ ID NO: 33, and SEQ ID NO: 40 to pod wall color.

| Haplotype | Pod Wall | SEQ ID NO: 26 | SEQ ID NO: 33 | SEQ ID NO: 40 | Number of Soybean Lines | Score |
|---|---|---|---|---|---|---|
| 1 | BR | AA | GG | AA | 1324 | 1.2 |
| 2 | BR | AA | GG | GG | 87 | 1.1 |
| 3 | MX | AA | GT | AG | 37 | 1.6 |
| 4 | MX | AA | GT | GG | 21 | 1.3 |
| 5 | MX | AA | TT | AA | 39 | 1.6 |
| 6 | MX | AA | TT | GG | 573 | 2.2 |
| 7 | MX | TT | GG | AA | 25 | 2.6 |
| 8 | TN | TT | TT | AA | 171 | 2.9 |
| 9 | TN | TT | TT | GG | 94 | 2.7 |

A second marker-association study was conducted on the L2 locus for pod wall color on a set of 308 soybean lines. An analysis of variance indicated that six molecular markers, SEQ ID NO: 47, SEQ ID NO: 48, SEQ ID NO: 49, SEQ ID NO: 50, SEQ ID NO: 51, and SEQ ID NO: 52, were highly significantly associated with pod wall color (P<0.001). When the three markers were combined into a haplotype, a distinct haplotype were associated with brown pod walls and another haplotype was associated with tan pod walls (Table 20).

TABLE 20

The relationship of haplotypes for the molecular markers SEQ ID NO: 47, SEQ ID NO: 48, SEQ ID NO: 49, SEQ ID NO: 50, SEQ ID NO: 51, and SEQ ID NO: 52 to pod wall color.

| Haplotype | Pod Wall Color | SEQ ID NO: 47 | SEQ ID NO: 48 | SEQ ID NO: 49 | SEQ ID NO: 50 | SEQ ID NO: 51 | SEQ ID NO: 52 | Number of Soybean Lines Evaluated |
|---|---|---|---|---|---|---|---|---|
| 1 | BR | TT | AA | CC | TT | TT | GG | 190 |
| 2 | TN | AA | TT | AA | GG | CC | AA | 118 |

Haplotype 1 is with brown pod wall color. Haplotype 2 is associated with tan wall color.

Example 8. Uses for Molecular Markers Associated with Flower, Pubescence, Hilum, and Pod Wall Color The major morphological traits assess by seed certifying agencies are flower, pubescence, hilum, and pod wall color. As mentioned earlier, misclassification of these key seed lot purity traits in soybean can greatly delay the certification process and cost the seed producer financially. The invention is also useful in the process of soybean breeding.

Having illustrated and described the principles of the present invention, it should be apparent to persons skilled in the art that the invention can be modified in arrangement and detail without departing from such principles.

APPENDIX TO THE SPECIFICATION

TABLE 14

| Locus/ Display Name (1) | Linkage Group (LG) (Chromosome) (2) | Source (3) | Start Base (4) | End Base (5) | Additional Locus Information (6) |
| --- | --- | --- | --- | --- | --- |
| AI973910 | LG K (9) | Glycine_max_release_2 | 42256806 | 42258847 | COP8-like protein [*Lilium longiflorum* (Trumpet lily)] (SEQ ID: 20) |
| BG045318 | LG K (9) | Glycine_soja_release_2 | 43505686 | 43506197 | Hypothetical protein At2g44140 [*Arabidopsis thaliana* (Mouse-ear cress)] (SEQ ID: 21) |
| AW459958 | LG N (3) | Glycine_max_release_2 | 460898 | 461355 | Multi antimicrobial extrusion protein MatE [*Medicago truncatula* (Barrel medic)] (SEQ ID: 27) |
| AW755424 | LG N (3) | Glycine_max_release_3 | 959341 | 961299 | OSJNBa0065O17.11 protein [*Oryza sativa (japonica cultivar-group)*] (SEQ ID: 28) |
| BF597543 | LG N (3) | Glycine_soja_release_2 | 557339 | 558689 | Putative co-chaperone CGE1 isoform b [*Oryza sativa (japonica cultivar-group)*] (SEQ ID: 34) |
| BU550813 | LG N (3) | Glycine_max_release_2 | 946496 | 947639 | Calmodulin binding heat shock protein [*Gossypium hirsutum* (Upland cotton)] (SEQ ID: 35) |
| BF597543 | LG N (3) | Glycine_soja_release_2 | 557339 | 558689 | Putative co-chaperone CGE1 isoform b [*Oryza sativa (japonica cultivar-group)*] (SEQ ID: 41) |
| TA53077_3847 | LG N (3) | Glycine_max_release_2 | 1713156 | 1716644 | Splicing factor-like protein [*Vitis riparia* (Frost grape) (*Vitis vulpina*)] (SEQ ID: 42) |

What is claimed is:

1. A method of molecular marker assisted soybean breeding, the method comprising the steps of:
   a) genotyping two parental soybean plants to determine the allelic state of each parental soybean plant with regard to each of:
      (i) whether the parental soybean plant comprises the W1 Locus "DD" allelic form (W1 allele) represented by SEQ ID NO:1 or the W1 Locus "II" allelic form (w1 allele) represented by SEQ ID NO:2;
      (ii) whether the parental soybean plant comprises the T Locus "CC" or "TT" allelic form of the molecular marker represented by SEQ ID NO:8 (M0243191);
      (iii) whether the parental soybean plant comprises the Td Locus "II" allelic form represented by SEQ ID NO:13 or the Td Locus "DD" allelic form represented by SEQ ID NO:14;
      (iv) whether the parental soybean plant comprises the R locus "AA" or "TT" allelic form of the molecular marker represented by SEQ ID NO:19 (M0100925); and
      (v) for the haplotype defined by the molecular markers represented by SEQ ID NO:26 (M0202726), SEQ ID NO:33 (M0119618), and SEQ ID NO:40 (M0094170), whether the parental soybean plant comprises the L2 Locus "AA" or "TT" allelic form of the molecular marker represented by SEQ ID NO:26 (M0202726), whether the parental soybean plant comprises the L2 Locus "AA" or "TT" allelic form of the molecular marker represented by SEQ ID NO:33 (M0119618), and whether the parental soybean plant comprises the L2 Locus "AA" or "GG" allelic form of the molecular marker represented by SEQ ID NO:40 (M0094170);
   b) crossing the two parental soybean plants genotyped in step (a) to generate an $F_1$ population of soybean plants;
   c) obtaining a DNA or RNA sample from a tissue of at least one $F_1$ soybean plant of the $F_1$ population generated by the cross in step (b);
   d) determining by a nucleic acid based analyses, for at least the allelic forms in step (a) that differ between the two crossed parental plants, the allelic state of the $F_1$ soybean plant; and
   e) selecting based on the determination of allelic state in step d an $F_1$ soybean plant for use in a soybean breeding program that is a true $F_1$ soybean plant and not the result of self-pollination of one of the parental soybean plants.

2. The method of claim 1, further comprising:
   (f) self-crossing the true $F_1$ soybean plant selected in step (e) to generate an $F_2$ population of soybean plants;
   (g) obtaining a DNA or RNA sample from a tissue of at least one soybean plant of the $F_2$ population generated by the cross in step (f) and:
      (i) determining whether the allelic state of the $F_2$ soybean plant comprises the W1 Locus "DD" allelic form (W1 allele) represented by SEQ ID NO:1 or the W1 Locus "II" allelic form (w1 allele) represented by SEQ ID NO:2;
      (ii) determining whether the allelic state of the $F_2$ soybean plant comprises the T Locus "CC" or "TT" allelic form of the molecular marker represented by SEQ ID NO:8 (M0243191);
      (iii) determining whether the allelic state of the $F_2$ soybean plant comprises the Td Locus "II" allelic form represented by SEQ ID NO:13 or the Td Locus "DD" allelic form represented by SEQ ID NO:14;
      (iv) determining whether the allelic state of the $F_2$ soybean plant comprises the R locus "AA" or "TT" allelic form of the molecular marker represented by SEQ ID NO:19 (M0100925); and
      (v) determining the allelic state for the haplotype defined by the molecular markers represented by SEQ ID NO:26 (M0202726), SEQ ID NO:33 (M0119618), and SEQ ID NO:40 (M0094170), whether the $F_2$ soybean plant comprises the L2 Locus "AA" or "TT" allelic form of the molecular marker represented by SEQ ID NO:26 (M0202726), whether the $F_2$ soybean plant comprises the L2 Locus "AA" or "TT" allelic form of the molecular marker represented by SEQ ID NO:33 (M0119618), and whether the $F_2$ soybean plant comprises the L2 Locus "AA" or "GG" allelic form of the molecular marker represented by SEQ ID NO:40 (M0094170); and
   (g) selecting based on at least the determination of allelic state in (i), (ii), (iii), (iv), and (v) an $F_2$ soybean plant that is homozygous and not segregating for the determined alleles.

3. The method of claim 2 further comprising self-crossing the selected $F_2$ soybean plant to generate an $F_3$ population of soybean plants.

4. The method of claim 3 further comprising determining the allelic state as determined in claim 2 of at least one generated $F_3$ plant or any progeny or descendent thereof in a successive generation to determine whether the seed lot purity traits of flower, pubescence, hilum, and pod wall color have been fixed and/or to validate visual observations of flower color, pubescence color, pod wall color, and hilum color.

* * * * *

SEQUENCE LISTING

<160> NUMBER OF SEQ ID NOS: 62

<210> SEQ ID NO 1
<211> LENGTH: 4657
<212> TYPE: DNA
<213> ORGANISM: Glycine max

<400> SEQUENCE: 1

```
ggcaactagc aaattaatta gcttcaccat ggactcattg ttacttctaa aagaaattgc      60
cacttccatt ttgatcttct tgatcactcg tctctccatt caaacattcc tcaaaagcta     120
tcgccagaaa ctcccaccgg ggccaaaagg gtgccagtt gtgggtgcac tccctctcat     180
gggaagcatg cctcatgtca ccttagcaaa gatggcaaaa aaatatggac ctataatgta     240
```

```
cctcaaaatg ggcactaaca acatggttgt ggcctctact ccagctgctg ctcgtgcctt      300
cctcaaaacc cttgatcaaa acttttcaaa ccggccctcc aatgctggtg caacccattt      360
ggcttatgat gcacgggtag gaatgcagca ccttcatatt ttttttttatt ttaaacacac     420 cattaatgtc acttattata taaactata cttttctttt gttttctctct ctcactaagt      480 gctaaataga attaaattaa cttatgaaga ggttagattc ggagaattct tataaattaa      540
ctttacataa attaatttta atttatagga gaaatttatt tattttctta ttttttctcc     600
tataagtatt tattataatt ttattcaaat tagcgcgtgt aaaaaaaaat aaatgaactg      660
atccaaaatt gaacaaaact ctgcttcgaa aaccgaacct ttttataaga acggttaggt     720
tttagagtgg ttcaacttgt ttctattcaa ttatttaatt agaaaaacct atccatatac     780
agtatagaat gaataattga cactaatgga accaaaccga agctaataaa atgtaaacca     840
ttttgaaaaa aatttaacta actcactta taaaaaaaaa aaattgatta accaaactgt      900
ttttatgagg tgatttgtaa atggaccggt ttggatttaa atacaaacca aatgtttcag     960
ggtcttaatc caaaatgag attattaaaa taagtgaatt cttctcttcc tctatctata     1020
tgtaataatt tttctaatat attaaaatac gtagctttat aatttactaa gataataaca     1080
tatgtatatc ttttcacttt tggctatttt ggatccgtcc ttgctgacag gatatggtgt     1140
ttgctcatta cggatcacgg tggaagttgc taagaaaact aagtaacttg cacatgcttg     1200
gaggaaaggc acttgatgat tgggcccaaa ttcgagatga agagatgggg cacatgcttg     1260
gtgcaatgta cgattgtaac aagagggatg aggctgtggt ggtggcggag atgttgacat     1320
attcaatggc caacatgatt ggccaagtta tattgagtcg tcgagtgttt gagacaaagg     1380
gttcggagtc taacgagttc aaggacatgg tggttgagct catgaccgtt gctggttact     1440
tcaacattgg tgacttcata cccttttttgg ccaagttgga cttgcaaggc atagagcgtg     1500
gcatgaagaa gttgcacaag aagtttgatg cgttgttaac gagcatgatt gaggagcatg     1560
ttgcttctag tcacaagaga aagggcaagc ccgatttctt agacatggta atggctcatc     1620
atagtgagaa ctccgatggg gaggaactat cgctcaccaa catcaaggca ctactcttgg     1680
tataacgctt tttatcttac ttctcaaatg tgtcattttc tttcttcatt tttattagac     1740
aaaaaaaaaa agtaaaatat ttgttatatg aggataacta ccatggagga tcacttatgg     1800
tatccaacgt tgttaaataa ccgttataat ccgccttaac gttataatgt ggcatttttc     1860 aaccccctctg cccatagaca gtttgtgagg gaggcccgtt atgacggcgc catagggtgc     1920
aatggcttcc taatatggag aaattttagc cttctgcata tgtcgtcatc tgtcattgat     1980
aactttggtg tggtgttaac aaaacaactt atatagttag gataggtagt aaaaagaaag     2040
tgttatttcc atattttttca aacccccttgt tatatatata tatagtggcg gacctacatg     2100
agtgataaaa aaatttattc tcttcataaa aaagtgtagg agggtacttg tacctcctta     2160 tttttttaaaa tttattaaat ttataaataa aattttatat ttttatattt tattttatct     2220
atatttatat aattgaattc attaatttta tttttttataa tttaaactcc ctaatttaaa     2280
atcttggatc cgcctatata tatatatcaa tcgttttttt acattttcaa gaattatatt     2340
aaaaacttca acatctttaa ttcaaaaatg ctatacactt tctaattcat tcttttaaac     2400
actttctaat tcatttttttt aaatatatta ttattgacta aaattgattg taaatcatac     2460
attggttcta ttttttttat tgaatgagtc tcacttgttc tgtggtttct aacatatttt     2520
aactaatatc aaagagtagg tacgttgagt gtattgttgg ttcaattctt ttctttttat     2580
```

```
aaaaaatttt gatatcataa tatttgaaag ttttgtttaa aataatcttc cctctatttg      2640
tacataatta tagcatgttt gttttggcaa attgaataaa aagtgaaaaa tttggaagca      2700
atataaaact tcgttagaac cattaaaaaa acataatcaa tttcccttcg ccaccccac       2760 acacatacat agtaaattta gtcctacaca tcataactta ttttgcctga aaaatgttga      2820
gttaattttt tatgacttga agtgacaaaa atacgttcaa aatttgttta tattgttcaa     2880
actataaatt tacaattgaa ccacaaagaa aaggatttc cgtatgacaa attaaaaatt      2940
aattgcgata ttgcatagtt aactctacta tacctgaatt tttatttgtt ttacaagtac     3000
aacttgttta tgatataagt ttagctataa gccaagtaag tacactttga atttagccaa     3060
aaaggaaatg ggcagtctgt atcataaatt ttcttagacg gaaatattaa agtacaagct     3120
acgaatatat cgtatatatt gtgtgagatc aacttaaatt aatcatgatg gaggttaaat     3180
gctgcaatta aattaaattc agcgggcctc tcccccaatt atttataacca acttttgct     3240 gcatttggaa ttggggccac ggaaagtaat gtcccaacta agaaaatatc ttctcatcat     3300
ttggtattgt acgtagtgaa tcacattgac tatatatcat gtattaaatc tgatatgaga     3360
atatttattt tccatcttat tttctatatg cataataata ttagttttg tctagtatat      3420 atatcacatt tttaatacat aaataacaaa tttagtcaac acttttttt ttaaaaaaaa      3480 agacctaaaa ttttgtttac actagaaact aaatattaat tgttgtgact aaattacaat    3540
gtgaatataa taataccatc ataatagtgt tcaattttaa caaaaaaatc tatgttatat    3600
atagtgcaaa ttcaacgaat caatacaaat catattttat ataaaatttt attgatgatg    3660
taaatgttag tgcaagttat tacgatgata atttaatccc tcgcctcata atcataccac    3720
acaccaacat tttctagctt gagatttgt tctaacaact atatatgcta ttttgttcca    3780
gaacctattc accgcagaca ccgatacatc ttcaagtata atagagtggt ccttagccga    3840
gatgttgaag aagcccagca taatgaagaa ggctcatgaa gaaatggacc aagtcatagg    3900
aagggatcgc cgtctcaaag aatctgacat accaaagctt ccatacttcc aagccatttg    3960
caaagagacc tatagaaagc acccttcaac accctaaac ctgcctcgaa tctcatctga     4020
accgtgccaa gtgaatggtt actacattcc cgagaacact aggctgaatg tgaacatttg   4080
ggccatagga agagaccctg atgtgtggaa caatcctttg gagtttatgc ccgagaggtt   4140
tttgagtggg aagaatgcca aaattgaccc acgtgggaat gattttgagc ttattccatt   4200
tggtgctggg aggaggattt gtgcagggac taggatgggg attgtgttgg ttcactacat   4260
tttgggcact ttggtgcatt cgtttgattg gaagctaccc aatgggggaga gggagttaga   4320 catggaggag tcctttgggc ttgccttgca aaaaaggtt ccacttgctg ctttggttac    4380
ccctaggttg aatccaagtg cttacatttc ttagaattgg ttgggttcga atattccacca   4440 gctatgttct ctagccttat tttgttgtcc aatgattttg tggctgtggc tacataaata   4500
agtaatgttt gggttgcaca acctatttgt atttgtaagg ttctatgtta cttggaaatc    4560
cgttacccca ccacctgcaa ggctttgatt tttattcttc atggatctct aatttagctg   4620
tcttgttttg gtttaattat atttttaatt ctccctc                             4657

<210> SEQ ID NO 2
<211> LENGTH: 4713
<212> TYPE: DNA
<213> ORGANISM: Glycine max

<400> SEQUENCE: 2
ggcaactagc aaattaatta gcttcaccat ggactcattg ttacttctaa aagaaattgc       60
```

```
cacttccatt ttgatcttct tgatcactcg tctctccatt caaacattcc tcaaaagcta    120
tcgccagaaa ctcccaccgg ggccaaaagg gtggccagtt gtgggtgcac tccctctcat    180
gggaagcatg cctcatgtca ccttagcaaa gatggcaaaa aaatatggac ctataatgta    240
cctcaaaatg ggcactaaca acatggttgt ggcctctact ccagctgctg ctcgtgcctt    300
cctcaaaacc cttgatcaaa acttttcaaa ccggccctcc aatgctggtg caacccattt    360
ggcttatgat gcacgggtag gaatgcagca ccttcatatt tttatttatt ttaaacacac    420
cattaatgtc acttattata tataactata cttctttttt gttttctctc tcactaagt    480 gctaaataga aataaattaa cttatgaaga ggttagattc ggagaattct tataaattaa    540
ctttacataa attaatttta atttatagga gaaatttatt tattttctta ttttttttctc   600 ctataagtat ttattataat tttattcaaa ttagcgcgtg taaaaaaaaa taatgaact    660 gatccaaaat tgaacaaaac tctgcttcga aaaccgaacc ttttttaataa gaacggttag    720 gttttagagt ggttcaactt gtttctattc aattatttaa ttagaaaaac ctatccatat    780
acagtataga atgaataatt gacactaatg gaaccaaacc gaagctaata aaatgtaaac    840
cattttgaaa aaaatttaac taactcactt tataaaaaaa aaaattgatt aaccaaactg    900
tttttatgag gtgatttgta aatggaccgg tttggattta aatacaaacc aaatgtttca    960
gggtcttaat ccaaaaatga gattcttaaa ataagtgaat tcttctcttc ctctatctat   1020
atgtaataat ttttctaata tattaaaata cgtagcttta taatttacta agataataac   1080
atatgtatat cttttcactt ttggctatt tggatccgtc cttgttgaca ggatatggtg     1140
tttgctcatt acggatcacg gtggaagttg ctaagaaaac taagtaactt gcacatgctt   1200
ggaggaaagg cacttgatga ttgggcccaa attcgagatg aagagatggg gcacatgctt   1260
ggtgcaatgt acgattgtaa caagagggat gaggctgtgg tggtggcgga gatgttgaca   1320
tattcaatgg ccaacatgat tggccaagtt atattgagtc gtcgagtgtt tgagacaaag   1380
ggttcggagt ctaacgagtt caaggacatg gtggttgagc tcatgaccgt tgctggttac   1440
ttcaacattg gtgacttcat acccttttg gccaagttgg acttgcaagg catagagcgt    1500
ggcatgaaga agttgcacaa gaagtttgat gcgttgttaa cgagcatgat tgaggagcat    1560
gttgcttcta gtcacaagag aaagggcaag cccgatttct tagacatggt aatggctcat    1620
catagtgaga actccgatgg ggaggaacta tcgctcacca acatcaaggc actactcttg    1680
gtataacgct ttttatctta cttctcaaat gtgtcatttt ctttcttcat ttttattaga    1740 caaaaaaaa aaagtaaaat atttgttata tgaggataac taccatggag gatcacttat    1800
ggtatccaac gttgttaaat aaccgttata atccgcctta acgttataat gtggcatttt    1860
tcaacccctc tgcccataga cagtttgtga gggaggcccg ttatgacggc gccatagggt    1920
gcaatggctt cctaatatgg agaaattta gccttctgca tatgtcgtca tctgtcattg    1980
gtaactttgg tgtggtgtta acaaaacaac ttatatagtt aggataggta gtaaaaagaa    2040
agtgttattt ccatatttt caaacccctt gttatatata tatatagtgg cggacctaca    2100
tgagtgataa aaaatttat tctcttcata aaaagtgta ggagggtact tgtacctcct     2160 tatttttaa aatttattaa atttataaat aaaatttat attttatat tatttttat       2220 ctatatttat ataattgaat tcattaattt tatttttat aatttaaact ccctaattta    2280
aaatcttgga tccgcctata tatatatatc aatcgttttt ttacattttc aagaattata   2340
ttaaaaactt caacatcttt aattcaaaaa tgctatacac tttctaattc attcttttaa   2400
```

```
acactttcta attcattttt ttaaatatat tattattgac taaaattgat tgtaaatcat    2460
acattggttc tatttttttt attgaatgag tctcacttgt tctgtggctt ctaacatact    2520
ttaactaata tcaaagagta ggtacgttga gtgtattgtt ggttcaattc tttttctttt    2580
ataaaaaatt ttgatatcat aatatttgaa agttttgttt aaaataatct tccctctatt    2640
tgtacataat tatagcatgt ttgttttggc aaattgaata aaaagtgaaa aatttggaag    2700
caatataaaa cttcgttaga accattaaaa aacataatc aatttcccctt cgccacccccc   2760 acacacatac atagtaaatt tagtcctaca catcataact tattttgcct gaaaaatgtt    2820
gagttaattt ttatgacttg aagtgacaaa aatacgttca aaatttgttt atattgttca    2880
aactataaat ttacaattga accacaaaga aaaaggatt tccgtatgac aaaattaaaaa    2940 ttaattgcga tattgcatag ttaactctac tatatctgaa ttttttatttg ttttacaagt   3000 acaacttgtt tatgatataa gtttagctat aagccaagta agtacactttt aaatttagcc   3060 aaaaaggaaa tgggcagtct gtatcataaa ttttcttaga cggaaatatt aaagtacaag    3120
ctacgaatat atcgtatata ttgtgtgaga tcaacttaaa ttaatcatga tggaggttaa    3180
atgctgcaat taaattaaat tcagcgggcc tctcccccaa ttatttatac caactttttg    3240
ctgcatttgg aattggggcc acggaaagta atgtcccaac taagaaaata tcttctcatc    3300
atttggtatt gtacgtagtg aatcacattg actatatatc atgtattaaa tctgatatga    3360
gaatatttat tttccatctt atttctata tgcataataa tattagtttt tgtctagtat     3420
atatatcaca tttttaatac ataaataaca aatttagtca acacttttttt tttaaaaaaa   3480 aaaagaccta aaatttttgtt tacactagaa actaaatatt aattgttgtg actaaattac    3540
aatgtgaata taataatacc atcataatag tgttcaattt taacaaaaaa atctatgtta    3600
tatatagtgc aaattcaacg aatcaataca aatcatattt tatataaaaa tttattgatg    3660
atgtaaatgt tagtgcaagt tattacgatg ataatttaat ccctcgcctc ataatcatac    3720
cacacaccaa cattttctag cttgagattt tgttctaaca actatatatg ctatttttgtt   3780 ccagaaccta ttcaccgcag gcaccgatac atcttcaagt ataatagagt ggtccttagc    3840
cgagatgttg aagaagccca gcataatgaa gaaggctcat gaagaaatgg accaagtcat    3900
aggaagggat cgccgtctca aagaatctga cataccaaag cttccctact tccaagccat    3960
ttgcaaagag acctatagaa agcacccttc aacaccccta aacctgcctc gaatctcatc    4020
tgaaccgtgc caagtgaatg gttactacat tcccgagaac actaggctga atgtgaacat    4080
ttgggccata ggaagagacc ctgatgtgtg gaacaatcct ttggagttta tgcccgagag    4140 gttttttgagt gggaagaatg ccaaaattga cccacgtggg aatgattttg agcttattcc    4200
atttggtgct gggaggagga tttgtgcagg gactaggatt ttgagcttat tccatttggt    4260
tcactacatt ttgggcttat tccattttttg agcttattcc atttggttca ctacattttg    4320
ggcactttgg tgcattcgtt tgattggaag ctacccaatg gggtgaggga gttagacatg    4380
gaggagtcct ttgggcttgc cttgcaaaaa aaggttccac ttgctgcttt ggttacccct    4440
aggttgaacc caagtgctta catttcttag aattggttgg gttcgaatat tcaccagcta    4500
tgttctctag ccttattttg ttgtccaatg attttgtggc tgtggctaca taaataagta    4560
atgtttgggt tgcacaacct atttgtattt gtaaggttct atgttacttg gaaatccgtt    4620
accccaccac ctgcaaggct tagatttttta ttcttcatgg atctctaatt tagctgtctt    4680
gttttggttt aattatattt ttaattctcc ctc                                 4713
```

<210> SEQ ID NO 3
<211> LENGTH: 10
<212> TYPE: DNA
<213> ORGANISM: Glycine max

<400> SEQUENCE: 3
ggggattgtg                                                              10

<210> SEQ ID NO 4
<211> LENGTH: 22
<212> TYPE: DNA
<213> ORGANISM: Glycine max

<400> SEQUENCE: 4
gaggatttgt gcagggacta gg                                                22

<210> SEQ ID NO 5
<211> LENGTH: 22
<212> TYPE: DNA
<213> ORGANISM: Glycine max

<400> SEQUENCE: 5
gggtagcttc caatcaaacg aa                                                22

<210> SEQ ID NO 6
<211> LENGTH: 21
<212> TYPE: DNA
<213> ORGANISM: Glycine max

<400> SEQUENCE: 6
ttgagcttat tccatttggt t                                                 21

<210> SEQ ID NO 7
<211> LENGTH: 20
<212> TYPE: DNA
<213> ORGANISM: Glycine max

<400> SEQUENCE: 7
actaggatgg ggattgtgtt                                                   20

<210> SEQ ID NO 8
<211> LENGTH: 254
<212> TYPE: DNA
<213> ORGANISM: Glycine max

<400> SEQUENCE: 8
cagttcttga agattcatga ctctaatttc agcagccggc caccgaacgc cggcgcgaaa       60
tatatagctt ataactacca agatctggtg tttgcyccct acggcccacg ctggcgattg      120
ctccggaaac tcacctccgt tcacctcttc tccggcaagg ccatgaatga atttagacac      180
ttgcgtcagg aagaggtagc tagattgaca tgcaacttgg caagttcaga cacaaaagca      240
gtgaatttgg gaca                                                        254

<210> SEQ ID NO 9
<211> LENGTH: 24
<212> TYPE: DNA
<213> ORGANISM: Glycine max

<400> SEQUENCE: 9
gccggcgcga aatatatagc ttat                                              24

<210> SEQ ID NO 10

```
<211> LENGTH: 20
<212> TYPE: DNA
<213> ORGANISM: Glycine max

<400> SEQUENCE: 10
gtgagtttcc ggagcaatcg                                              20

<210> SEQ ID NO 11
<211> LENGTH: 18
<212> TYPE: DNA
<213> ORGANISM: Glycine max

<400> SEQUENCE: 11
ctggtgtttg cccccctac                                               18

<210> SEQ ID NO 12
<211> LENGTH: 17
<212> TYPE: DNA
<213> ORGANISM: Glycine max

<400> SEQUENCE: 12
tggtgtttgc tccctac                                                 17

<210> SEQ ID NO 13
<211> LENGTH: 505
<212> TYPE: DNA
<213> ORGANISM: Glycine max

<400> SEQUENCE: 13
tttaattaga gaatatttga atgagaatgt taaataaaat atttttagta ttccttatag    60
ttacttttat atttgacgag aaatttccaa tgctgtaaac acgtactaag aatttctccc   120
aaaaaaaaac tcgttctaag aaattaaaac aaaaataaac atattttaac tagcatactt   180
ggcgcactcg ctactcgtta accctacgta catcaataaa aaacattttt taagaagcag   240
tattcacatg tgattttggc tttgattgca tgagcacgag taacgtgcct cttgttcttc   300
ttcttgttct ttttcaaata aaaaggttct cccacgcgtt ggtagcgcgt gaaaagaatc   360
gacgagtcac gcaaattgtg cggctcccat caatagtaat actcaatact caccctccat   420
gaaaacgaac acgtttccga acatcacacg cgtttcacgt gccctatttg ggctctccgt   480
tccccacgtg tcttcatcta actca                                        505

<210> SEQ ID NO 14
<211> LENGTH: 494
<212> TYPE: DNA
<213> ORGANISM: Glycine max

<400> SEQUENCE: 14
tttaattaga gaatatttga atgagaatgt taaataaaat atttttagta ttccttatag    60
ttacttttat atttgacgag agatttccaa tgctgtaaac acgtactaag aatttctccc   120
aaaaaaaaac tcgttctaag aaattaaaac aaaaataaac atattttaac tagcatactt   180
ggcgcactcg ctactcatta accctacgta catcaataaa aaacattttt taagaagcag   240
tattcacatg tgattttggc tttgattgca tgagcacgag taacgtgcct cttgttcttt   300
ttcaaataaa aaggttctcc cacgcgttgg tagcgcgtga aaagaatcga cgagtcacgc   360
aaattgtgcg gctcccatca atagtaatac tcaatactca ccctccatga aaacgaacac   420
gtttccgaac atcacacgcg tttcacgtgc cctatttggg ctctccgttc cccacgtgtc   480
ttcatctaac tcat                                                    494
```

```
<210> SEQ ID NO 15
<211> LENGTH: 25
<212> TYPE: DNA
<213> ORGANISM: Glycine max

<400> SEQUENCE: 15
gctttgattg catgagcacg agtaa                                              25

<210> SEQ ID NO 16
<211> LENGTH: 21
<212> TYPE: DNA
<213> ORGANISM: Glycine max

<400> SEQUENCE: 16
cgctaccaac gcgtgggaga a                                                  21

<210> SEQ ID NO 17
<211> LENGTH: 21
<212> TYPE: DNA
<213> ORGANISM: Glycine max

<400> SEQUENCE: 17
tcttgttctt tttcaaataa a                                                  21

<210> SEQ ID NO 18
<211> LENGTH: 26
<212> TYPE: DNA
<213> ORGANISM: Glycine max

<400> SEQUENCE: 18
ttgttcttct tcttgttctt tttcaa                                             26

<210> SEQ ID NO 19
<211> LENGTH: 1293
<212> TYPE: DNA
<213> ORGANISM: Glycine max

<400> SEQUENCE: 19
agttcatagc cagtggacta taaggaaccg atgcagccat gatttctgct gcatgtggct        60
gccacaggga acttccacaa gagggaggtt catcctcaat tgatttgtgg atgcatttct       120
catccwacta tcacacacac acaaattact attgaggatt caaataaaga ctacattaaa       180
ataagatttt acaaattagt agttatatga aatataaagt ttaatagcat agttcgctac       240
aaattaagta ctgcatcatg aattcatgaa ctttgaagtc agagaaaaag aattttatgg       300
agcatatgac tctgaggttc attataagta tagaggagga aggtcttgct tcagttggta       360
ggcctaagtt tgtaacctga aattaaatac actgaaaata aataaaataa tattttgagt       420
aaatgttgaa atagtttta tttggagctt tacaggtgca ttgtctgcaa tcatccctaa       480
catcaaaata gtagctaaaa gttgggggca aagagtaaga cactatcttt tctataaaag       540
ttaaatacta caaaagaaaa atgaaaaata attaacaaca aaacactttt aacaccataa       600
ccaaacaacc agccatcaaa ttagtcatag catgaaactt caattctcta tatgctaact       660
acttcaaata gcatagtaaa gatcattata ttgtcatata cacacaaaaa aaggtggcat       720
aaaaaatcat attctatagg ctaattaaat gctacggaga tgggctttta tttaatgaaa       780
aagatgctct taatttgagt ggaggtgcta caatctgaat atgtggggtg ggaaggtctt       840
ctaaggggag gcttgaacag aaaagcctca atttggtgga gagatcaata tatcattgtc       900
```

```
ttgtggggga gatgatgaat ctgagtggtc tgatagtagc taaaattagt gacggtgagc      960
aagcaaggtt ttttggtttg acacatggtt aggtgatttt agtcatgttg aaaaatttcc     1020
cagattatat cttttatcac caaatcaaaa ggagagtgtt aaggagttca tgtgcttta     1080 ctgttaaatc agcgtatatg cagatgatct agtgggttcc tctcaaattg aggtgagatg    1140
aaacaagttt ggaagctata gtataaaaat tcaaccaaaa gggaattttc ttctgtggag    1200
attcatcttt acaagttact tacgaaagac aagatccaca attgcatttc tggcaacaca    1260
cactactaca cattaatcat gtggagggtg att                                 1293

<210> SEQ ID NO 20
<211> LENGTH: 552
<212> TYPE: DNA
<213> ORGANISM: Glycine max

<400> SEQUENCE: 20
agccataaaa tttatttgaa aaaaaatttg cttatttggc aggacgatga tgctgtcaat      60
gctgaagctt ttattaataa agcatcattc ttggtcagca acagtcagca tgaagttctg     120
aatttaaagt acaaggtttg ctatgcaagg attttggatt tgaagaggaa gttttggaa     180 gcagcattac gatattatga tatgtctcaa attgagaaaa ggcaaatagg agacgaggag    240
attaatgagg aagcacttga acaagcttta tctgctgctg ttacatgcac aatattggca    300
gctgcaggac ctcaacgttc ccgtgttctt gccactttgt acaaggatga gcggtgttca    360
aagttgaaga tctatccaat actgcagaag gtgtatttgg agagaattct cagaaaacca    420
gaaattgatg cttttgcaga agaattgaaa ccacatcagc aagctcttct tccagacaat    480
ttcactgtgc tggaccgcgc tatgattgag cacaatcttt tgagtgctag caaactctat    540
actaatatca gc                                                         552

<210> SEQ ID NO 21
<211> LENGTH: 235
<212> TYPE: DNA
<213> ORGANISM: Glycine max

<400> SEQUENCE: 21
gcttccaatg gctatttatg ttgtttctgg agatgaagat ggggagcgtg gtggagcacc      60
agttgtctgc attgaagatg cctccaaacg ctgttttgag ttttcaagtg cttagctgc     120 ttggacacct ctacttttat tggttccttt ggttcttgga cttgataaag tcaatccaag    180
gtatattcca ttattgcgct caacttttaa atttccccaa agccttggca tcatg         235

<210> SEQ ID NO 22
<211> LENGTH: 24
<212> TYPE: DNA
<213> ORGANISM: Glycine max

<400> SEQUENCE: 22
tgtggatgca tttctcatcc tact                                            24

<210> SEQ ID NO 23
<211> LENGTH: 29
<212> TYPE: DNA
<213> ORGANISM: Glycine max

<400> SEQUENCE: 23
gcagtactta atttgtagcg aactatgct                                       29
```

```
<210> SEQ ID NO 24
<211> LENGTH: 15
<212> TYPE: DNA
<213> ORGANISM: Glycine max

<400> SEQUENCE: 24
cacacacaca caaat                                                         15

<210> SEQ ID NO 25
<211> LENGTH: 15
<212> TYPE: DNA
<213> ORGANISM: Glycine max

<400> SEQUENCE: 25
cacactcaca caaat                                                         15

<210> SEQ ID NO 26
<211> LENGTH: 297
<212> TYPE: DNA
<213> ORGANISM: Glycine max

<400> SEQUENCE: 26
atagtgaaaa tggaatcgag cgttctggaa tgtctgggca tggagataat cggcgtgatg        60
agcccagtct cgatctgcat gttccttgtg gtcctgttag tgtattctct ctcctcgccg       120
tccaccacca ccactawcgc caccgctgcc aacctcgtct acgccgagaa ccccteegac       180 accaccgccc agaagctcga gggcgccgtc ctcaacgccg tggtcttcgt cgtcctcatc       240
gcgctcgtca ccttcctcct cgtcctcctc tactactaca actgcaccgc cttcctc         297

<210> SEQ ID NO 27
<211> LENGTH: 458
<212> TYPE: DNA
<213> ORGANISM: Glycine max

<400> SEQUENCE: 27
tggcaaatga acttggaaga ggaagctcaa aagatgcaaa gttctctata gttgtgacag        60
tgcttacatc cttttcaatt ggttttattt tatttgttct tttcttattt ttaagagaaa       120
aagtagctta tctctttact tcaaacgaag atgtggctac tgctgtgggg gatttgtcac       180
ctttgttagc agtttctttg ttactaaaca gtattcaacc tgtactctca ggtatgcttt       240
ataaatcttg gtgtcttggt ttaaagaact tttaatagtt taagatttga acctattgt        300 ttttacagtc tgaacgacat gaaattatat gatttcaata ggggtggctg ttggagcagg       360
gtggcaaagc attgtagcat atgtgaacat agggtgttat tacctcatag gtattccagt       420
tggaatagtg cttggtaaca ttattcactt gcaagtca                               458

<210> SEQ ID NO 28
<211> LENGTH: 479
<212> TYPE: DNA
<213> ORGANISM: Glycine max

<400> SEQUENCE: 28
ccacgcgtcc ggaattgaat tgcattgcat tgcttttgct gcgttgaaaa tccgaagaaa        60
tcgaattgca ttgctccgtg aaaaaaatgg aaagcgagaa agcgtttgag tttctcggat       120
gcgttcctct cctgcagagg cttccgagct cgtctctgag gaagatagct caacttgtgg       180
atgtcaaaca ttgtgagccc ggagagttat gtggtcgcga gggtgaaccc ggagatggtg       240
tgtacttcat attggatgga gaggctgagg ttcttggatc tgttagtgcc aatgatgaaa       300
```

```
atcgaccaga gttccaattg aaacaatatg actactttgg gtatggtttg gcaaacacaa      360
gtcaccaggc agatgtggat gctatggcta agcatgcatg cttagagctg gctcatgagc      420
actcaacact ggtggaggca agtctatct  ggagagcaga aaattctctc gagacatgc       479

<210> SEQ ID NO 29
<211> LENGTH: 22
<212> TYPE: DNA
<213> ORGANISM: Glycine max

<400> SEQUENCE: 29
aatcgagcgt tctggaatgt ct                                                22

<210> SEQ ID NO 30
<211> LENGTH: 21
<212> TYPE: DNA
<213> ORGANISM: Glycine max

<400> SEQUENCE: 30
cagatcgaga ctgggctcat c                                                 21

<210> SEQ ID NO 31
<211> LENGTH: 16
<212> TYPE: DNA
<213> ORGANISM: Glycine max

<400> SEQUENCE: 31
acgccgatta tctcca                                                       16

<210> SEQ ID NO 32
<211> LENGTH: 15
<212> TYPE: DNA
<213> ORGANISM: Glycine max

<400> SEQUENCE: 32
cgccgataat ctcca                                                        15

<210> SEQ ID NO 33
<211> LENGTH: 881
<212> TYPE: DNA
<213> ORGANISM: Glycine max
<220> FEATURE:
<221> NAME/KEY: unsure
<222> LOCATION: (1)..(881)
<223> OTHER INFORMATION: unsure at all n locations

<400> SEQUENCE: 33
tgtgcttgct ggtgtctttg gtacagctgc aactggatac atactccwac gaggtaagaa      60
tgctgctgct cttgcattca gaagcatatg cctttttttt taagagtctt gctaaccagt     120
agtccagtac cctaaaggca ttggttaaag aattaaaaga agaaagtatt tactgtgaaa     180
atcataggag gacgcaaaaa aagttatggg tgacacaatt ttttgcattc caataaaaat     240
atttctcctt ttatttcttt aaccactgcc ctaagggcac tggtttgcat ttgcctttt      300 taatggtaat tcgcttataa gtgatctcct gactgttgtg caggttcttg ggatgatgtt     360
tttaaggttg ctgttgcatt gtacataata ggcacattgg tctggaatat cttttcaact     420
ggagagaaaa ttcttgacta aagaatgtaa tgatgatgtg aatgaaggtg tgtgcagcat     480
gaggcttgcg ggttgnnggg gctgaggang ggaggggcgg cggggatggg gtggccgggt     540
ggggcggggg gctggggngg gggcggnggg ggcggggggcg gggggggggc gtgccgcctt     600
gctcgccggg tgcgctctcc ctgtccgtgc gtgcgctccg gccgctgcgg gtgcgcgttg     660
```

```
gccggccccg gcgccgcggc gcggggtcct ngtcctcccg gctcgctgcc ccctcccgc    720 ggggtctgtc cggtggtggt cgcccgtctc ttcccttgct ctgccccccc gcccgctctg    780
ttgcggtctc gtctcgcgcc tcgcccgtcn tcgcctcgtg gcggggcgcg tgtgtgggcc    840
ccccgcgtgt gttttcgtcc tggtgtgccg ggtggcttcg c                        881
```

<210> SEQ ID NO 34
<211> LENGTH: 493
<212> TYPE: DNA
<213> ORGANISM: Glycine max

<400> SEQUENCE: 34

```
ggggagagga caaataaac aacagctatc agagcatata taaacagttc attgaaattc      60
taaattcact tggagttgaa ccagtggaga cagttggaac acctttgat ccattgctac     120 atgaagcaat tatgcgcgag gattctgatg aatttgagga tggcatcata attcaagaat    180
tcagagaggg ttttaaactt ggtgagcgtc tcttgcgtcc gtcaatggtg aaggtatcag    240
ctggtccagg acctgcaaag cctgaacaag aagcaccgca agaagaacac ggcgacactg    300
aaatttctga ggacagtaaa caaaacgagg gcagcacaga aacagagtct tgaaaggtca    360 aaactttgc ctgatttcag ttttgcaata gtatatcaat tttaatctcc ctgaacataa     420
tgttggctgt aagagtctcc caggagatat tcctcccaaa tttcccttaa aaagaaagtt    480
attattctga gat                                                       493
```

<210> SEQ ID NO 35
<211> LENGTH: 594
<212> TYPE: DNA
<213> ORGANISM: Glycine max

<400> SEQUENCE: 35

```
cacaaataaa tagaaccata aaaggaagag agaaagaata aagcaattag taaggagcaa     60
agaagaagaa gaagaacaag caaatattgc tttactaagc tttgctaaaa agaaatattt    120
catggagatg tcttttttgaa caccatatga ccagcgtcat ccacatcaaa caggcgtcca    180
acaaattcat tccaactttg tgttcgtttc ttgtgaaaca aggaggaacc aagggcactt    240
gatcttccag aatcctcccc aacatcaatt tgatgaaatg ttccatatga tgaaggtgag    300
tatgcttgag gaatatccaa agcaactgct ctctgaaggg ctgcatggta ctcttcactg    360
tgttctcgag cgatagattc atgcctctcc atcctttgct ctgctggaat ctccatatgc    420
tcatcgttat ctcgcattat atcgagagcc cgtcgggatt ctctctctat ccaaatgatg    480
gcatggtcag aagttgcatt gcaagaaaga actaaatgct caaacctccc atcaacaggt    540
actgctgttc taacgacagg tggaagcctt cctatcctac aatcagaaga gact            594
```

<210> SEQ ID NO 36
<211> LENGTH: 24
<212> TYPE: DNA
<213> ORGANISM: Glycine max

<400> SEQUENCE: 36

```
tggtttgcat ttgcctttt taat                                              24
```

<210> SEQ ID NO 37
<211> LENGTH: 22
<212> TYPE: DNA
<213> ORGANISM: Glycine max

```
<400> SEQUENCE: 37
ccaagaacct gcacaacagt ca                                              22

<210> SEQ ID NO 38
<211> LENGTH: 17
<212> TYPE: DNA
<213> ORGANISM: Glycine max

<400> SEQUENCE: 38
cgcttataag tgatctc                                                    17

<210> SEQ ID NO 39
<211> LENGTH: 18
<212> TYPE: DNA
<213> ORGANISM: Glycine max

<400> SEQUENCE: 39
cgcttataag ttatctcc                                                   18

<210> SEQ ID NO 40
<211> LENGTH: 395
<212> TYPE: DNA
<213> ORGANISM: Glycine max

<400> SEQUENCE: 40
agctccctga gaacctcata ttctgcatca aaaacccatc ccgctgcctt caacaacccg     60
ttatgaacat aaccaccgtg aaattccgcc tgtcccagct tgttatcaag caaaactata    120
taatcacttt ccttccccaa attgagtcca ctaacagcca gtatgatttc agcatgatca    180
tgatcaaggt atatcatgta tggagtaacg cgaccttggt tatcgttgta gtctttacgc    240
aagataaccc aatctggatt aatgccataa cctccttggg gagcccattg agggttacga    300
atatcatctt cgtagacggc taagattagc cgacagatcc gaggcacrgg ctcaaattct    360
tgtgcagtag ccaggcccca attttcactc tcata                               395

<210> SEQ ID NO 41
<211> LENGTH: 493
<212> TYPE: DNA
<213> ORGANISM: Glycine max

<400> SEQUENCE: 41
ggggagagga caaataaac aacagctatc agagcatata taaacagttc attgaaattc      60
taaattcact tggagttgaa ccagtggaga cagttggaac acccttttgat ccattgctac   120 atgaagcaat tatgcgcgag gattctgatg aatttgagga tggcatcata attcaagaat    180
tcagagaggg ttttaaactt ggtgagcgtc tcttgcgtcc gtcaatggtg aaggtatcag    240
ctggtccagg acctgcaaag cctgaacaag aagcaccgca agaagaacac ggcgacactg    300
aaatttctga ggacagtaaa caaaacgagg gcagcacaga aacagagtct tgaaaggtca    360
aaacttttgc ctgatttcag ttttgcaata gtatatcaat tttaatctcc ctgaacataa    420
tgttggctgt aagagtctcc caggagatat tcctcccaaa tttcccttaa aaagaaagtt    480
attattctga gat                                                      493

<210> SEQ ID NO 42
<211> LENGTH: 449
<212> TYPE: DNA
<213> ORGANISM: Glycine max

<400> SEQUENCE: 42
```

```
gcacgagaca atttcttgcc actgtaattt ttcgtctcct tggtagccgg gttgtgcatg    60
aggatgcaga catttcggtg aatgctgtgc catttctgcc tataagggag gcagagtcat   120
cttctgaagt tgcttctgct gcttttgtgg attcttcttc tgggagtttg tttgatcgtt   180
tgttgttggt tttgcatgga ttattaagta gttatccacc aagttggctt agggcaaagc   240
ctgtttcaaa gacaatcagt gaacctacga gggaaatttc tggaattgac cgagaattgt   300
tggaggcttt gcagaatgac ttggatcgta tgcaactgcc agacactatt cggtggcgta   360
tccaagctgc aatgcccatg ctcattccct ctatgcggtg ctctttatcc tgccagccac   420
catctgtttc aaattctgct cttgtttgc                                     449
```

<210> SEQ ID NO 43
<211> LENGTH: 22
<212> TYPE: DNA
<213> ORGANISM: Glycine max

<400> SEQUENCE: 43

```
acggctaaga ttagccgaca ga                                             22
```

<210> SEQ ID NO 44
<211> LENGTH: 20
<212> TYPE: DNA
<213> ORGANISM: Glycine max

<400> SEQUENCE: 44

```
ggcctggcta ctgcacaaga                                                20
```

<210> SEQ ID NO 45
<211> LENGTH: 14
<212> TYPE: DNA
<213> ORGANISM: Glycine max

<400> SEQUENCE: 45

```
tgagcctgtg cctc                                                      14
```

<210> SEQ ID NO 46
<211> LENGTH: 13
<212> TYPE: DNA
<213> ORGANISM: Glycine max

<400> SEQUENCE: 46

```
tgagcccgtg cct                                                       13
```

<210> SEQ ID NO 47
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 47

```
acctccgtgt tgttaaaatt gaaccccttt ttttctcatt naatttgtta tnatcgattc    60
tatccgtttt accttgtttc tacacccat gattgttttc cttgttttct ctccacaaac   120
cacctccact gtgaacctcc gcaaaaatct ggtaacacca ccttgaattc cttatcattt   180
gtcgtgttta ctccctcttg waacctcaat tagacctggt taggtgattg gtttcaaaga   240
agcaaaggta gagggtgttg agaggaagaa gaatggttgt tgctgttgca ccgtnagcaa   300
```

```
c                                                                   301

<210> SEQ ID NO 48
<211> LENGTH: 301
<212> TYPE: DNA
<213> ORGANISM: Glycine max

<400> SEQUENCE: 48
cacgcataat aagaagacat ggcaacccaa attttgcagc aatgggtgtt aaaactgttg    60
caattgacca ccatacaact ccaaaaccta gtactagctt cccaccaagt ttgtctgccc   120
atatgccacc aacgatctat accaaaaaaa aagcattcaa tcaatatgaa agtaatgtca   180
ttagaatctt tcatgcacgc wggacgaaat gaagagacag tttgaagatc agaacatgct   240
gagattgcta gcatatactg tttaagaaca gaataggcta tggcatgttc aaccagcagt   300
g                                                                   301

<210> SEQ ID NO 49
<211> LENGTH: 301
<212> TYPE: DNA
<213> ORGANISM: Glycine max

<400> SEQUENCE: 49
aaattaatac ttttatttt aaaaatgtta ttaaaaatta taaaaaaaaa gtgaatacaa     60
aagagagatt tgaaaataag ctaaaccaac acttattata caaaagtgga gaatgttgat   120
ttgtcaaatg tataaattgg ttcatgttcg acgaccagca aaatctttat tgtgttccat   180
ttttagttgg ttggtttcag mtgaaaacgg ttggtcctgc cattttttgct tttgtcaaaa   240 ggactaaaat gtattaaaca tgcaacaaga tcttgagatt ccatgtgaca caagagataa   300
g                                                                   301

<210> SEQ ID NO 50
<211> LENGTH: 301
<212> TYPE: DNA
<213> ORGANISM: Glycine max

<400> SEQUENCE: 50
tgtgaattgt gattatgtga atacaaactg ttttcgagtg ctcggtttta aacgagttgt    60
tttagcattt taatgactct ctggtctagt tttctcctca atctctttga tgatggagat   120
tgtagggagg gattgtggat tcagaattga cagcatgcgc atgcatgacc tatcaattaa   180
ataacaggga gtttcagggg kgaatgtctc tttctagata ttcttttaaa acatttgata   240
ttctttgaaa gcctttgaca tgcatgtggc tcatacaact ctgtgcatta tcttctcctt   300
g                                                                   301

<210> SEQ ID NO 51
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 51
taaaaaatgt ttantgtctt gaaaatataa aaaagacatt caatacttat tatccaatta    60
gtaataagaa gatattgaaa gaagattnac aattattgtt gtacaataca aataatgcaa   120
tgtttaggga caaatagatg ggtccttcga attcccttng gccgaacatg gncttcgata   180
```

```
tgttttcac ttttcttga yttagtcaga atttccctgt acgtggctct ctcactttga      240
actagataaa gctagtgggg ttcatgatcc attcgcccct aatttgattt aggttgaagt    300
t                                                                    301

<210> SEQ ID NO 52
<211> LENGTH: 301
<212> TYPE: DNA
<213> ORGANISM: Glycine max

<400> SEQUENCE: 52
attagtatat tacacaaaat tagcatactc ttaagtctaa caaacttaga cctctctgct    60
gcaaaagcta taaacacatc acctatgaga tgattatgag taaaaaaaat ttacttcagt   120
acacaaccaa gcactgtgac atggaatcta aaaaggcaa cataaaacaa tttagcacgc    180
aacctctaaa acttaagcaa rcattgagca acaccacag catcattgaa ggtgcagatc   240
atctttccac aatgaaaact caaatcaaat caaatacaaa acacacacat acttttaaaa  300
a                                                                    301

<210> SEQ ID NO 53
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 53
ccatttgagt gaaaatgacc caatggaacg gtgagctcaa gnaatgcaaa caaggaaact    60
taatagcatt tcatttgaag tccgcaggga tataatatat aataacgagg gtattaaaaa   120
gtgttttgac actatttctc gggataagga cctatatgtt nggccataac tagcctgcac   180
tttgaaatct atttcagttt kaattttgaa agtgagtgtg gcgtaccgtg tacgtatctg   240
cagaaagtga atgaatggta atgggggaag aagggtgcaa ggtatgtgtt acaggaggcn   300
g                                                                    301

<210> SEQ ID NO 54
<211> LENGTH: 301
<212> TYPE: DNA
<213> ORGANISM: Glycine max

<400> SEQUENCE: 54
ttgaagaaag gggtagagag aggattgacc cctttgcca ttggaagcct gatgtgcagg    60
gaatccttga acaaggaatc tgtgatagaa gaagtagtac aagcagcact ggattctgtt   120
cttcctggca caagtgaagc tacattgctg gattctgttt cccaaatcct ggacttgcac   180
ctcgatgaga ttgtcagatc ycattttataa tagcattgaa ttctgcaatg gtagctggta   240
tatacatgtc agtgtgtaca tatgttcacg tacatatgta tagctcaaat aattggattt   300
t                                                                    301

<210> SEQ ID NO 55
<211> LENGTH: 301
<212> TYPE: DNA
<213> ORGANISM: Glycine max
<220> FEATURE:
<221> NAME/KEY: unsure
<222> LOCATION: (1)..(301)
```

<223> OTHER INFORMATION: unsure at all n locations

<400> SEQUENCE: 55

```
tattgattat aaatttataa atgttaaaaa aaaaaaaaag agaaaanaaa gaattgaagt      60
tgtggttggt agtaaaccag caccaggcga acaagtggac acaatttacc tacaagtaac     120
taaccaaccg gaagcacagg ctacaacggt cctttcacac ccggtctcaa agcttttaaa     180
aacgaacaca tacgcactca yatttccatt ccacctcaac aaaacacaaca acactctctc    240
ttctcgctct tggcttttcg ctcttcactc actctcattc attcatttcc accgttcatg     300
g                                                                     301
```

<210> SEQ ID NO 56
<211> LENGTH: 301
<212> TYPE: DNA
<213> ORGANISM: Glycine max

<400> SEQUENCE: 56

```
tatttacata atttctttta catggtatta atcttttttt gttttacca atagtagaat       60
ttataatatt atattagact taaaaatagt agtattatac agaatcacac tctctcaaat    120
taagcacata ggagaaatca ccaacgtgac agctaataat tgccaaatat aatattaaca    180
aggtggtttt atataaactc yggttggacc ccaaaaagaa atacccaaat atcacttttg    240
gactattgcg ggtttgcgaa aaataacaaa tgcagtgctt atttaatccg tgtgagtgtg    300
t                                                                     301
```

<210> SEQ ID NO 57
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 57

```
ttcaaaatcn attagttttg catatcttta aagtatagtt gtgaaacntg atttggtctg     60
attagttaat tttgcatatc tttaaagtat agtagtgaaa cctgattcaa ttcgatcaat    120
tgagctggtc tgatcatgat ctaatatttt aattggattg gtttcactat tgaattaatt    180
atgcaattga cttagnatga yctatccgat taggtattgg atcccggttg aacagatctc    240
attgatttta aaaaaaaat cattttgaac tcttattagt attaattgtt attttagatt     300
t                                                                    301
```

<210> SEQ ID NO 58
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 58

```
agtaacatgc agcgctatcc acgtcatcct catggttccc tacataaccc tgtcctgtaa     60
cctgttggtc ctttcaacta aaaactctgc tccttttgtt attacgttta ccactcaatt    120
ttttctccag caacttcagg tgcatgtatt catgctcaat ttcatctctg tctcactcga    180
attaattgat taattanccg aattctgtat tggtggctaa ccttcgatga gaaggttctg    240
```

```
cattgtgttt tcatttttg gattgcattg aaattttgnt gttgaacaga gaatgagttg    300
t                                                                   301

<210> SEQ ID NO 59
<211> LENGTH: 301
<212> TYPE: DNA
<213> ORGANISM: Glycine max

<400> SEQUENCE: 59
tgccaccgtg aatatgcaag ctgccatttt ctctagagag agagataagt gattttgatg    60
tgaagagaga aaagaaaaga aaagtaaacg cacgaaaggt atcaccgtca ctcacatctc   120
acatgaacat agaatgttgt gttgtgtctg agtctgaggt aacaaatgga atcgacgagt   180
gagtgaggtg tcaaaagtta aaagagttgc tgtcagacac ttcacattag attcctcggt   240
gattcactta tcgaaagagg acagtattca aggatgaaaa cttttatttt aattttttc    300 t                                                                   301

<210> SEQ ID NO 60
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 60
cattcctatg tagttatggt atacaatgac atttcaataa tttcaacagg gcaattattn    60 cacacaatt ttaaataagg aacttcttca caccaacgga atacggaacc aaccaatttt   120
tagaaatata caaaagcact actggttaag gatgaatatc tacagctata cagtgaattc   180
aaaatataaa aggaagtgaa atcaatgata aggtctagat tcggctggag gaaccaaagt   240
aagagtacgt gtgtcgcatt gcatgtccac gtcttaaaac tttttttct tctgaaaatt    300 c                                                                   301

<210> SEQ ID NO 61
<211> LENGTH: 301
<212> TYPE: DNA
<213> ORGANISM: Glycine max
<220> FEATURE:
<221> NAME/KEY: unsure
<222> LOCATION: (1)..(301)
<223> OTHER INFORMATION: unsure at all n locations

<400> SEQUENCE: 61
aattaaatct ctaaaagatt tatcaaacaa atnatatctt aaaatatcat taatttatca    60
tcattgtcat aactgttatc atcaccgtca ttatgactgt tgtcgttgtc actgtcacca   120
ccattgttgg atgatagcga cgatgatgac aacaatcatg acgatggtgg tggtgacaga   180
ggtgaaaatc ataatgattt ttgcaatgtt agtaactact gcaataatga aggtcatgac   240
agtagaggtg gtgatagttg acgacgatga tggtgataac agcgacgatt atggtggtga   300
c                                                                   301

<210> SEQ ID NO 62
<211> LENGTH: 301
<212> TYPE: DNA
<213> ORGANISM: Glycine max
```

```
<400> SEQUENCE: 62
gttttgtaga gtcttaaaat gatcgtatgg aacaacattt gcctatggtt accaacatat        60
aaatcaacta atgatgctgt aatatataga cagctagcac gtaaacaacg ttttggaata       120
gcaagttgtg aggtatatgt agctccaaac tcacagtggg atgtttttc tctttatgca       180 ctgatgatac atgttcccgt aaaaaatttg attttttct gctgaaaaat ttagatggat       240
tgactcttgg aattcattgg tgttagattt aagattcaaa aatacttata aaaatattta      300
t                                                                      301
```